United States Patent
Moore et al.

(10) Patent No.: US 12,039,884 B2
(45) Date of Patent: Jul. 16, 2024

(54) SIMULATION OF MINIMALLY INVASIVE SURGERY PROCEDURES

(71) Applicant: Howmedica Osteonics Corp., Mahwah, NJ (US)

(72) Inventors: Jesse G. Moore, Germantown, TN (US); Joseph Ryan Woodard, Memphis, TN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 17/917,090

(22) PCT Filed: Apr. 9, 2021

(86) PCT No.: PCT/US2021/026665
§ 371 (c)(1),
(2) Date: Oct. 5, 2022

(87) PCT Pub. No.: WO2021/207661
PCT Pub. Date: Oct. 14, 2021

(65) Prior Publication Data
US 2023/0117814 A1    Apr. 20, 2023

Related U.S. Application Data

(60) Provisional application No. 63/008,339, filed on Apr. 10, 2020, provisional application No. 63/008,349, filed on Apr. 10, 2020.

(51) Int. Cl.
*G09B 23/30* (2006.01)
*G16H 40/63* (2018.01)

(52) U.S. Cl.
CPC ............. *G09B 23/30* (2013.01); *G16H 40/63* (2018.01)

(58) Field of Classification Search
CPC .................... G09B 23/28; G09B 23/30–34
See application file for complete search history.

(56) References Cited

U.S. PATENT DOCUMENTS

| 5,769,640 A | 6/1998 | Jacobus et al. |
| 9,990,862 B2 | 6/2018 | Choi |

(Continued)

FOREIGN PATENT DOCUMENTS

WO    1999042978 A1    8/1999

OTHER PUBLICATIONS

"ARTHRO Mentor," Product Brochure, 3D Systems, Inc., 2019 (Applicant points out, in accordance with MPEP 609.04 (a), that the year of publication, 2019, is sufficiently earlier than the effective U.S. filing date, so that the particular month of publication is not in issue.) 4 pp.

(Continued)

*Primary Examiner* — Kang Hu
*Assistant Examiner* — Correll T French
(74) *Attorney, Agent, or Firm* — Shumaker & Sieffert, P.A.

(57) ABSTRACT

In some examples, a simulator system may simulate one or more minimally invasive surgery (MIS) procedures associated with bone removal. The simulator system comprises an input device configured to detect a position of a portion of a user tool relative to an operation envelope, a simulation device defining one or more surfaces that define one or more boundaries for a movement of the user tool relative to the operation envelope during a simulated surgical procedure, and processing circuitry. The processing circuitry is configured to receive, from the input device, information indicative of the position of at least the portion of the user tool relative to the operational envelope, generate a performance metric based on the position of at least the portion of the user (Continued)

tool relative to the operational envelope over a period of time, and output, for display to a user, the performance metric.

20 Claims, 10 Drawing Sheets

(56) References Cited

U.S. PATENT DOCUMENTS

| | | | |
|---|---|---|---|
| 10,016,243 B2 | 7/2018 | Esterberg | |
| 2005/0137609 A1* | 6/2005 | Guiraudon | A61B 17/3423 606/108 |
| 2010/0086905 A1* | 4/2010 | Illana Alejandro | G09B 23/285 434/262 |
| 2010/0167249 A1* | 7/2010 | Ryan | G09B 23/285 434/267 |
| 2010/0167253 A1* | 7/2010 | Ryan | G09B 23/30 434/272 |
| 2016/0225288 A1* | 8/2016 | East | A61B 17/1671 |
| 2018/0353308 A1* | 12/2018 | Tompkins | A61F 2/585 |
| 2019/0142520 A1 | 5/2019 | VanDyken | |
| 2020/0078093 A1* | 3/2020 | Bohl | G16H 30/40 |

OTHER PUBLICATIONS

ARTHRO Mentor Platform, retrieved from https://simbionix.com/simulators/arthro-mentor/arthro-mentor-platforms/ on Jan. 17, 2023, 2 pp.

Bissonnette, "Artificial Intelligence Distinguishes Surgical Training Levels in a Virtual Reality Spinal Task", Journal of Bone and Joint Surgery, vol. 101-A, No. 23, Dec. 2019, 8 pp.

International Preliminary Report on Patentability from International Application No. PCT/US2021/026665 dated Oct. 20, 2022, 9 pp.

International Search Report and Written Opinion of International Application No. PCT/US2021/026665, dated Jul. 30, 2021, 11 pp.

Response to Communication Pursuant to Rules 161(1) and 162 EPC dated Nov. 17, 2022, from counterpart European Application No. 21722343.7, filed May 15, 2023, 17 pp.

\* cited by examiner

SIMULATION OF MINIMALLY INVASIVE SURGERY PROCEDURES

This application is a national stage application under 35 U.S.C. § 371 of PCT Application No. PCT/US2021/026665, filed Apr. 9, 2021, which claims the benefit of U.S. Provisional Patent Application No. 63/008,339, filed on Apr. 10, 2020, and claims the benefit of U.S. Provisional Patent Application No. 63/008,349, filed on Apr. 10, 2020. The entire content of each of these applications is incorporated herein by reference.

TECHNICAL FIELD

This disclosure relates to medical procedures, and, more specifically, systems and techniques for simulating medical procedures.

BACKGROUND

Surgical joint repair procedures involve repair and/or replacement of a damaged or diseased joint. A surgical joint repair procedure, such as joint arthroplasty as an example, may involve replacing the damaged joint with a prosthetic that is implanted into the patient's bone. Surgeons may practice joint repair procedures on cadavers or other anatomical models.

SUMMARY

This disclosure describes a variety of systems, devices, and techniques for simulating one or more minimally invasive surgery (MIS) procedures, such as arthroscopic surgery procedures. For example, a simulator system may track one or both of a position a movement of a user tool relative to an operation envelope. Additionally, the simulator system may compare one or both of the position of the user tool the and movement of the user tool to virtual anatomy and expected movements for a respective simulated procedure. The simulated procedure may mimic a corresponding authentic procedure. The simulator system may provide feedback during the simulated procedure, the feedback may include haptic feedback that is applied to the user tool based on one or both of the position of the user tool and the movement of the user tool. Additionally, in some cases, the feedback may include visual feedback and audio feedback.

In some examples, a simulator system simulates one or more orthopedic procedures. The simulator system includes: an input device configured to detect a position of a portion of a user tool relative to an operation envelope; a simulation device defining one or more surfaces that define one or more boundaries for a movement of the user tool relative to the operation envelope during a simulated surgical procedure; and processing circuitry. The processing circuitry is configured to: receive, from the input device, information indicative of the position of at least the portion of the user tool relative to the operational envelope; generate a performance metric based on the position of at least the portion of the user tool relative to the operational envelope over a period of time; and output, for display to a user, the performance metric.

In some examples, a method for simulating one or more orthopedic procedures includes detecting, by an input device, a position of a portion of a user tool relative to an operation envelope, where a simulation device defines one or more surfaces that define one or more boundaries for a movement of the user tool relative to the operation envelope during a simulated surgical procedure; receiving, by processing circuitry, information indicative of the position of at least the portion of the user tool relative to the operational envelope from the input device; generating, by the processing circuitry, a performance metric based on the position of at least the portion of the user tool relative to the operational envelope over a period of time; and outputting, by the processing circuitry for display to a user, the performance metric.

In some examples, a computer-readable storage medium stores instructions that, when executed, cause one or more processors to: detect a position of a portion of a user tool relative to an operation envelope, where a simulation device defines one or more surfaces that define one or more boundaries for a movement of the user tool relative to the operation envelope during a simulated surgical procedure; receive information indicative of the position of at least the portion of the user tool relative to the operational envelope from an input device; generate a performance metric based on the position of at least the portion of the user tool relative to the operational envelope over a period of time; and output, for display to a user, the performance metric.

In some examples, a simulator system simulates one or more orthopedic procedures. The simulator system includes an input device configured to detect a position of at least a portion of a user tool relative to an operation envelope; a haptic device configured to apply haptic feedback to the user tool; and processing circuitry. The processing circuitry is configured to: determine a virtual boundary for the user tool relative to the operation envelope, the virtual boundary representing a portion of a virtual bone; receive information indicative of the position of the portion of the user tool relative to the operation envelope; control, based on the position of the portion of the user tool relative to the operation envelope in relation to the virtual boundary, the haptic device to apply haptic feedback to the user tool; and receive user input that at least one of enables or disables control of the haptic device to apply haptic feedback to the user tool based on the position in relation to the virtual boundary.

In some examples, a method of simulating one or more orthopedic procedures includes detecting, by an input device, a position of at least a portion of a user tool relative to an operation envelope; applying, by a haptic device, haptic feedback to the user tool; determining, by processing circuitry, a virtual boundary for the user tool relative to the operation envelope, the virtual boundary representing a portion of a virtual bone; receiving, by the processing circuitry, information indicative of the position of the portion of the user tool relative to the operation envelope; controlling, by the processing circuitry and based on the position of the portion of the user tool relative to the operation envelope in relation to the virtual boundary, the haptic device to apply haptic feedback to the user tool; and receiving, by the processing circuitry, user input that at least one of enables or disables control of the haptic device to apply haptic feedback to the user tool based on the position in relation to the virtual boundary.

In some examples, a computer-readable storage medium stores instructions that, when executed, cause one or more processors to: determine a virtual boundary for a user tool relative to the operation envelope, the virtual boundary representing a portion of a virtual bone; receive, from an input device configured to detect a position of at least a portion of the user tool relative to the operation envelope, information indicative of the position of the portion of the user tool relative to the operation envelope; control, based on the position of the portion of the user tool relative to the operation envelope in relation to the virtual boundary, a haptic device to apply haptic feedback to the user tool; and receive user input that at least one of enables or disables control of the haptic device to apply haptic feedback to the user tool based on the position in relation to the virtual boundary.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
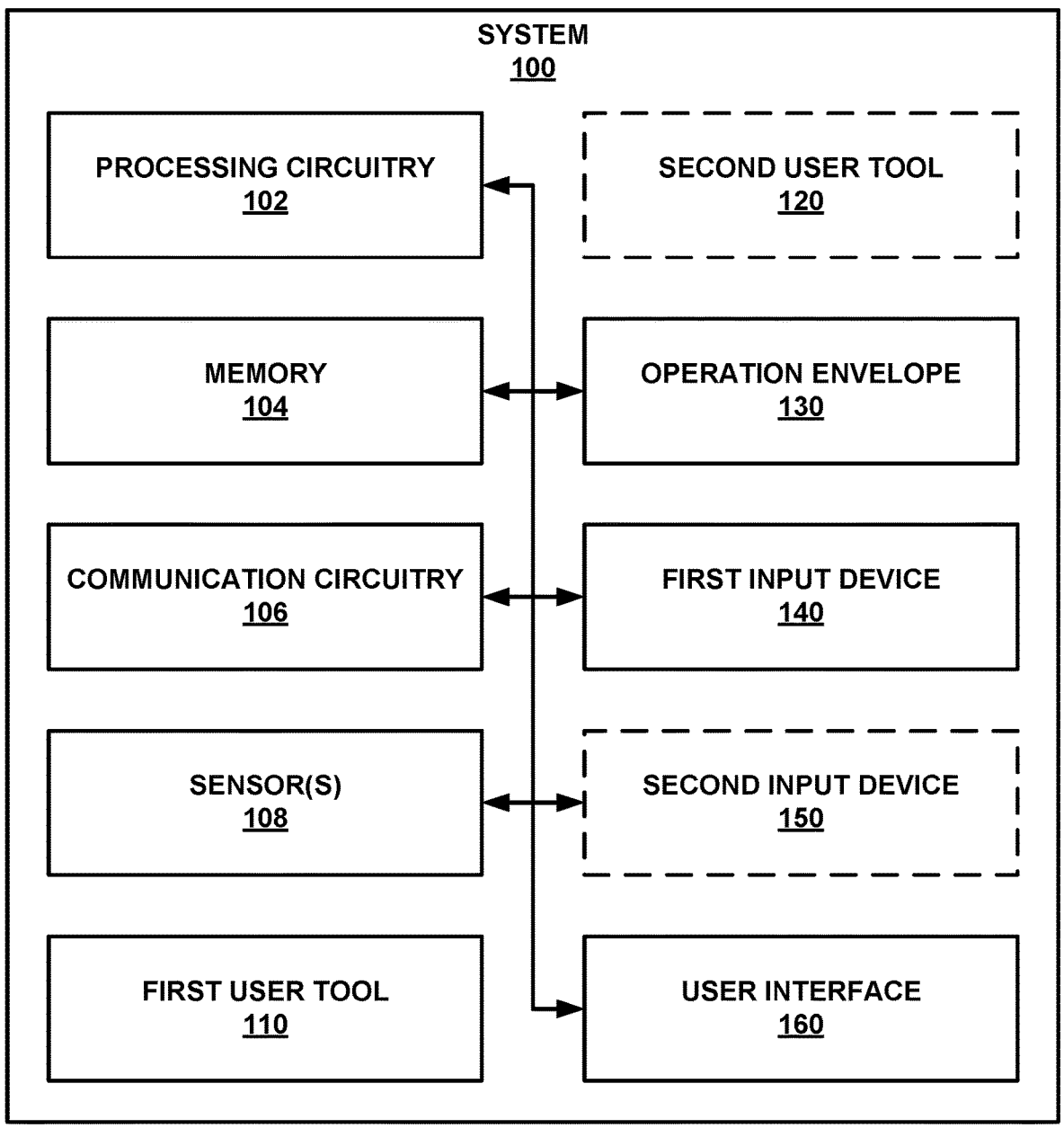
FIG. 1 is a block diagram illustrating a system for simulating one or more MIS procedures, in accordance with one or more techniques of this disclosure.

This disclosure describes a variety of systems, devices, and techniques for simulating one or more minimally invasive surgery (MIS) procedures, such as arthroscopic surgery procedures. Arthroscopic surgery procedures can involve manipulating one or more surgical tools to create incisions, insert objects (e.g., arthroscopes, medical implants, trocars) into the incisions, carve sections of bone, remove cartilage, or any combination thereof. Arthroscopic surgical procedures generally limit the ability of a physician to directly see the surgical tool in relation to the target tissue (e.g., a bone). In addition, some procedures, such as bone carving, may require the physician to perform certain movements that are specific to the species in question (i.e., humans). Although the physician may benefit from practice performing these procedures, physicians may have limited access to cadavers. In addition, even if a physician can practice with a cadaver, it may be difficult and/or time consuming for the physician to evaluate the accuracy of the practiced procedure.

As described herein, a simulator system may imitate an environment of an authentic surgical procedure, thus allowing a user (e.g., a surgeon) to perform a corresponding simulated procedure which enables the user to develop skills for performing the authentic procedure in an actual patient. The simulator system may include, in some examples, an operation envelope including a set of apertures configured to receive one or more user tools. The operation envelope may include a wall that represents a boundary of an enclosed space, where the set of apertures are formed in the wall. In this way, the wall of the operation envelope may be a representation of the skin of a human patient and the set of apertures may represent incisions that can be made during a variety of arthroscopic surgery procedures that the simulator system is configured to simulate. The operation envelope may thus be a partial or full structure, in some examples, within which the user may perform a simulated procedure. During a simulated procedure, a user tool of the one or more user tools may be inserted into an aperture of the set of apertures and maneuvered within the enclosed space bounded by the wall of the operation envelope similar to a way in which a surgical tool is maneuvered within a joint of a human patient during an authentic procedure corresponding to the simulated procedure. The simulator system may be configured to provide feedback to the user throughout the duration of the simulated procedure. Such feedback may include haptic feedback, audio feedback, visual feedback, or any combination thereof. Haptic feedback may be in the form of mechanical stimulus (e.g., vibrations of varying amplitude or frequencies) and/or forces that prevent the user tool from moving in one or more directions within the operation envelope. Although the simulated procedure is generally described as being performed within the operation envelope, the system may track the user tool in any location relative to the operation envelope. For example, the system may even track the user tool or any other structure or action outside of the envelope or merely relative to one or more locations.

FIG. 1 is a block diagram illustrating a system 100 for simulating one or more MIS procedures, in accordance with one or more techniques of this disclosure. As seen in FIG. 1, system 100 includes processing circuitry 102, memory 104, communication circuitry 106, sensor(s) 108, first user tool 110, operation envelope 130, first input device 140 and user interface 160. Additionally, in some examples, system 100 includes second user tool 120 and second input device 150.

Processing circuitry 102, in one example, may include one or more processors that are configured to implement functionality and/or process instructions for execution within system 100. For example, processing circuitry 102 may be capable of processing instructions stored in memory 104. Processing circuitry 102 may include, for example, microprocessors, digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 102 may include any suitable structure, whether in hardware, software, firmware, or any combination thereof, to perform the functions ascribed herein to processing circuitry 102.

Memory 104 may be configured to store information within system 100 during operation. Memory 104 may include a computer-readable storage medium or computer-readable storage device. In some examples, memory 104 includes one or more of a short-term memory or a long-term memory. Memory 104 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, memory 104 is used to store data indicative of instructions for execution by processing circuitry 102.

Communication circuitry 106 may include any suitable hardware, firmware, software or any combination thereof for communicating with one or more remote devices (e.g., one or more devices that are not a part of system 100). Under the control of processing circuitry 102, communication circuitry 106 may receive downlink telemetry from, as well as send uplink telemetry to the one or more remote devices. Communication circuitry 106 may include any combination of a Bluetooth® radio, an electronic oscillator, frequency modulation circuitry, frequency demodulation circuitry, amplifier circuitry, and power switches such as a metal-oxide-semiconductor field-effect transistors (MOSFET), a bipolar junction transistor (BJT), an insulated-gate bipolar transistor (IGBT), a junction field effect transistor (JFET), or another element that uses voltage or current for its control.

In some examples, processing circuitry 102 is electrically coupled to sensor(s) 108. Sensor(s) 108 may include any combination of motion sensors, optical sensors, accelerometers, temperature sensors, chemical sensors, and pressure sensors. Sensor(s) 108 may, for example, sense a position, a velocity, or an acceleration of first user tool 110 in relation to operation envelope 130. In some examples, one or more sensors 108 may be affixed to first input device 140 and/or second input device 150. In other examples, one or more sensors 108 may be disposed within, or configured to sense the space within, an operation envelope within which first user tool 110 and/or second user tool 120 can be moved.

System 100 may include, or be configured to attach to, devices that allow a user, such as a surgeon, to perform one or more simulated procedures. For example, a simulated surgical procedure may correspond to an authentic surgical procedure to be performed the user on human patients. In some examples, the simulated surgical procedure may be a simulated procedure on a human bone. In this way, system 100 may enable the user to acquire skills for performing authentic surgical procedures. In some examples, system 100 includes a user tool (e.g., first user tool 110) configured to be controlled by the user.

First user tool 110 may include an elongated member configured to be held, gripped, or otherwise handled by the user during a simulated surgical procedure. First user tool 110 may represent one or more surgical tools that are used in an authentic surgical procedure that corresponds to the simulated surgical procedure. First user tool 110 may include features that allow the user to handle first user tool 110 during the simulated surgical procedure similar to how the user handles surgical tools during the corresponding authentic surgical procedure. For example, each user tool of first user tool 110 may include a weight and a set of dimensions (e.g., a length, a width, one or more circumferences, or any combination thereof) that are similar to a surgical tool that first user tool 110 is configured to mimic. In this way, first user tool 110 may be represented by a user tool of a set of user tools, where each user tool of the set of user tools being designed to mimic one or more surgical tools that are used during an authentic surgical procedure corresponding to a simulated surgical procedure that a user may perform using system 100. In some examples, one or more electrical connections may exist between user tool 110 and other components of system 100, such as operation envelope 130. In some examples, no electrical connections exist between user tool 110 and other components of system 100.

Figure 2:
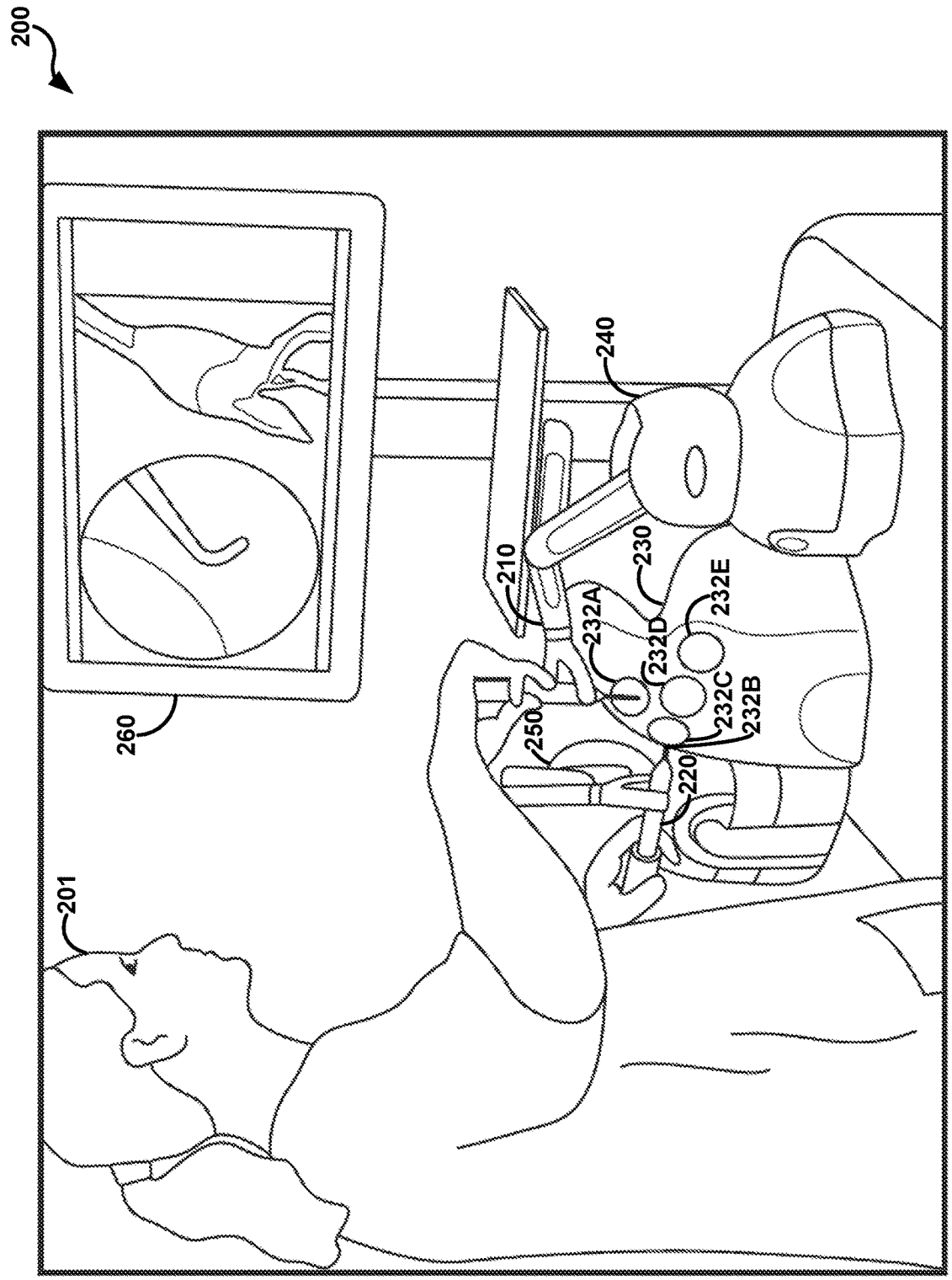
FIG. 2 is a schematic diagram illustrating a system which is an example of the system of FIG. 1, in accordance with one or more techniques of this disclosure.

Operation envelope 130 may be configured to receive first user tool 110 via one or more apertures (e.g., aperture 232A of FIG. 2). Operation envelope 130 may include a wall that represents a boundary of an operation space, and the one or more apertures may be formed in the wall of operation envelope 130. In some examples, the operation space may represent an enclosed space. In some examples, the operation space may represent an open space. The wall of operation envelope 130 may, in some cases, cause operation envelope 130 to resemble a human joint such as an ankle, a knee, a hip, a wrist, an elbow, or a shoulder, one or more bones, soft tissue (e.g., connective tissue and/or muscle) or any other tissue or collection of tissues of interest for a procedure. In this way, the wall can be configured to mimic a shape of a skin surface of a patient such that operation envelope 130 provides a realistic representation of the respective joint. In some cases, the wall of operation envelope 130 may cause operation envelope 130 to resemble a generic shape such as a cube, a sphere, or any custom or irregular shape having straight and/or curved boundaries. Since first user tool 110 may correspond to one or more surgical tools and the one or more apertures are configured to receive first user tool 110, the one or more apertures may correspond to incisions that are made during an authentic surgical procedure corresponding to a simulated surgical procedure that the user may perform using system 100. For example, the one or more apertures may be placed at locations on the wall of operation envelope 130 corresponding to locations on the skin of a human patient that incisions are made during the authentic surgical procedure.

In some examples, the enclosed space that is bounded by the wall of operation envelope 130 includes an "open" space that does not include objects which obstruct a movement of first user tool 110 within the enclosed space. At least some of sensor(s) 108 may be placed on and/or inside of operation envelope 130 in order to generate data which represents a position of first user tool 110 within operation envelope 130 during the simulated medical procedure. In other examples, the operation envelope can be open at some portions or entirely open instead of having a specific wall or boundary. Although operation envelope 130 is generally described as referring to a two dimensional or three dimensional physical envelope, operation envelope 130 or any other operation envelope described herein may have more dimensions. For example, operation envelope 130 may include a time dimension for tracking user tool movement and/or movement of the simulated anatomy (e.g., heart beats, lung movement, etc.).

First input device 140 may be configured to interact with first user tool 110 during the simulated medical procedure. For example, first input device 140 may be configured to apply a force (e.g., haptic feedback) to a user tool of first user tool 110 based on a first set of control parameters generated by processing circuitry 102. Processing circuitry 102 may generate the first set of control parameters based on the data generated by sensor(s) 108 that indicates the position of first user tool 110 within the enclosed space. For example, processing circuitry 102 may receive the data (e.g., information) indicative of a position of the user tool within the enclosed space from at least one of sensor(s) 108. In some examples, processing circuitry 102 may receive the data indicative of the position of the user tool within the operation envelope 130 from at least one sensor which generates data indicative of a position of a set of electrical motors which control a movement of first input device 140. Although electrical motors are generally described herein, other types of motors (e.g., pneumatic or chemical motors), brakes, cables, or any other mechanism for applying a force to first input device 140 may be used to control movement of first input device 140 or any other device described herein. In some examples, the sensors which generate data indicative of the position of the set of electrical motors are a part of sensor(s) 108. In turn, processing circuitry 102 may generate, based on the position of first user tool 110 within the enclosed space, a first set of control parameters for controlling the input device. In some cases, to generate the first set of control parameters, processing circuitry 102 may compare the position of first user tool 110 within the enclosed space with a target position of first user tool 110 within the enclosed space. Sensor(s) 108 may include any type of electrical, mechanical, optical, or chemical sensors, such as joint encoders, transducers (e.g., a linear displacement transducer), hall sensors (or other magnetic type sensors), strain gauges, spring pin indicators, optical sensors (e.g., a Fabry-Perot interferometer), or any other types of sensors may be used herein. As opposed to, or in addition to, motors or other dynamic feedback options for preventing the user from moving away from a target location, the first user input device 140 (e.g., the physical arm attached to the user tool), may include physical stops (that may be adjustable) that prevent certain range of motion of the user tool when attached.

The target position of user tool 110 may represent a position of first user tool 110 that conforms to a simulated surgical procedure that may be performed by moving first user tool 110 in relation to operation envelope 130. For example, the target position of first user tool 110 within the enclosed space may represent a target position of first user tool 110 within the enclosed space that changes over a period of time, the target position changing according to the simulated surgical procedure. As such, the target position of the user tool 110 within the enclosed space over the period of time may be a simulation of an authentic surgical procedure to be performed on a human patient. The target position may be defined by one or more boundaries that delineate whether the user tool is, or is not, in the target position (e.g., the correct side of the boundary). In some examples, the target position may also, or alternatively, include an orientation of user tool 110 with respect to the one or more boundaries, one or more axes of user tool 110, one or more planes, depth of penetration, or any other target position of the tool and/or cutting surface of the tool pertinent to the use of user tool 110 during the procedure. The one or more boundaries may be planar, curved, or any irregular shape. In some examples, the one or more boundaries may define a completely enclosed space or an at least partially open space. In other examples, the target position may be a specific target position in space that is a line, a plane, a point in space, or other such target positions. Processing circuitry 102 may track the deviation or distance that the user tool is from the target position, where the deviation below a threshold distance from the target position may be acceptable for the procedure.

In some examples, processing circuitry 102 may determine that the position of first user tool 110 within the enclosed space is displaced from the target position of first user tool 110 within the enclosed space by greater than a threshold distance. The target position of first user tool 110 may be stored by memory 104. In some cases, to determine that the position of first user tool 110 is displaced from the target position of first user tool 110, processing circuitry 102 may determine that a point one or more points on first user tool 110 is displaced from a target position of the respective point of the one or more points. In some cases, to determine that the position of first user tool 110 is displaced from the target position of first user tool 110, processing circuitry 102 may determine that an axis of user tool 110 is displaced from a target position of the axis. The threshold distance may change as the target position changes in space during the procedure such that the acceptable volume for the user tool can increase or decrease as the user tool moves through space for the procedure.

In some examples, one or more haptic devices (not illustrated in FIG. 1) prevent the first user tool 110 from being displaced from the target position of first user tool 110 by greater than the threshold distance. The one or more haptic devices may in some examples, represent electrical motors which control a movement of first input device 140 which applies haptic feedback to first user tool 110. For example, first input device 140 may apply a force to first user tool 110 in order to prevent first user tool 110 from being displaced from the target position of first user tool 110 by greater than the threshold distance. For example, processing circuitry 102 may output information that causes first input device 140 to apply the force to first user tool 110 in order to prevent first user tool 110 from being displaced from the target position of first user tool 110 by greater than the threshold distance. In response to a force being applied to first user tool 110 which would otherwise move the position of first user tool 110 past the target position of first user tool 110, first input device 140 may apply an opposing force which prevents a movement of first user tool 110 past the target position. In some examples, first user tool 110 includes a set of joints, where a haptic device (e.g., electric motor) controls movement at each joint of the set of joints. Additionally, each joint of the set of joints may include a sensor which is configured to generate information indicative of a position of the respective joint (e.g., a position of the respective haptic device).

In some examples, system 100 may calculate spring forces or otherwise dynamically adjust the forces applied to first user tool 110 as user tool 110 approaches a boundary (e.g., increase the force as first user tool 110 gets closer to a boundary), to simulate procession through different densities of bone or soft tissue, or any other simulation purpose. In addition, or alternatively, first input device 140 may be configured to provide a guiding force that assists user tool 110 into the correct path or position. This guiding force would then be a positive force acting in the direction of the target position, as opposed to a force that prevents user tool 110 from moving away from the target position (i.e., a negative force). In some examples, system 100 may be configured to receive user input that turns on or off one or both of positive or negative forces that can assist the user during the simulated procedure. Instead of, or in addition to applying forces, system 100 may visually display arrows (or other visual indicators), sounds, or other feedback to the user that indicates to the user in which direction the user should move user tool 110 in order to follow the procedure. System 100 may also adjust the force feedback to the user based on different bone densities, boundaries of different types of tissues, etc. For example, cortical bone is much more dense than cancellous bone on the inside of the bone. Therefore, system 100 may change the force feedback as the user moves user tool 100 through the different areas of the bone. System 100 may also adjust the force feedback based on a simulation of tool sharpness or dullness changes during the procedure, heat buildup, velocity of user tool 110 movement through the simulated tissue, etc. These force feedback may help to simulate conditions that may cause bone fracture, for example, due to inappropriate movements or speed of user tool 110.

Processing circuitry 102 may, in some cases, control first input device 140 to apply haptic feedback to first user tool 110 in order to prevent first user tool 110 from being displaced from the target position of first user tool 110 by greater than the threshold distance based on the joint position information generated by the respective sensor located at each joint of the first user tool 110. In some cases, processing circuitry 102 may control first input device 140 to apply haptic feedback to first user tool 110 in order to prevent first user tool 110 from being displaced from the target position of first user tool 110 by greater than the threshold distance based on a position of first user tool 110 as determined using information generated by sensor(s) 108.

In some examples, in response to determining that the position of first user tool 110 is displaced from the target position of first user tool 110 by greater than the threshold distance, processing circuitry 102 is configured to generate the first set of control parameters, where the first set of control parameters are generated to cause first input device 140 to guide first user tool 110 to approach the target position of first user tool 110 within the enclosed space. For example, the user may handle first user tool 110 during a simulated surgical procedure that is performed using system 100. First input device 140 may be mechanically connected to first user tool 110 during the simulated surgical procedure and first input device 140 may move according to the first set of control parameters generated by processing circuitry 102 in order to apply pressures to first user tool 110. Based on the position of first user tool 110 being displaced from the target position of first user tool 110 by greater than the threshold distance, processing circuitry 102 may generate the first set of control parameters and output the first set of control parameters to the first input device 140. In turn, the first input device 140 may apply the control parameters to move first user tool 110 towards the target position of user tool 110.

In some examples, in response to determining that the position of first user tool 110 is displaced from the target position of the user tool by greater than the threshold distance, processing circuitry 102 is configured to generate the first set of control parameters to cause one or more haptic devices to cause first input device 110 to apply a mechanical stimulus to first user tool 110. The mechanical stimulus indicates to the user that the position of the user tool is displaced from the target position of the user tool by greater than the threshold distance. In some examples, the mechanical stimulus represents an example of haptic feedback indicating to the user that the position of first user tool 110 is displaced from the target position of first user tool 110 by greater than the threshold distance. In turn, the user may correct the position of first user tool 110 to be closer to the target position of first user tool 110. In some examples, the mechanical stimulus represents a mechanical vibration, a mechanical pulsing, or another kind of mechanical movement.

In some examples, processing circuitry 102 may execute one or more artificial intelligence (AI) algorithms (e.g., a machine learning model) to generate control parameters for haptic devices of first input device 140 and/or second input device 150. For example, a computing device may generate the one or more AI algorithms based on a set of training data which includes data indicative of a set of simulated procedures and/or a data obtained from real surgical procedures. In some examples, the set of simulated procedures may be performed using system 100. In some examples, an inputs to the one or more AI algorithms may be a position of one or both of first user tool 110 and second user tool 120 as a function of time during a simulated procedure. An output to the one or more AI algorithms may be a performance metric, one or more suggestions for improvement, a set of data indicating locations and times in which one or both of first user tool 110 and second user tool 120 deviates outside of a virtual boundary, or any combination thereof. In some examples, the one or more AI algorithms may generate the output in real time as the simulated procedure occurs. In some examples, the one or more AI algorithms may generate the output after the simulated procedure is completed. In this manner, processing circuitry 102 may utilize one or more AI algorithms to provide control of a user tool (e.g., using haptic feedback) and/or performance information regarding the level of success of the user during the stimulated procedure.

In some examples, processing circuitry 102 may track the position of first user tool 110 within the enclosed space for a period of time. Subsequently, processing circuitry 102 may generate, based on the position of first user tool 110 within the enclosed space over the period of time, a performance metric indicating a performance level of a user that is performing a simulated surgical procedure using system 100. For example, a first performance metric may result from a first performance of a simulated surgery procedure and a second performance metric may result from a second performance of the simulated surgery procedure. If a position of first user tool 110 deviates from the target position of first user tool 110 during the first performance of the simulated surgery procedure more than a position of first user tool 110 deviates from the target position of first user tool 110 during the second performance of the simulated surgery procedure, the second performance metric may indicate a higher-quality performance level than the first performance metric. As such, the performance metric may be correlated with an amount of deviance of the position of first user tool 110 from the target position of first user tool 110. In some examples, processing circuitry 102 may track the amount of time the user took to complete part of or the entire procedure, display the amount (volume) of bone removed, a location of an inserted implant, representations of the tissue (e.g., bone) after the simulated procedure, or any other aspects of the procedure.

In some examples, processing circuitry 102 calculates the performance metric based on any one or combination of a distance between the position of first user tool 110 from the target position of first user tool 110, a number of times that the position of first user tool 110 deviates from the target position of first user tool 110 by more than a threshold distance, and a total amount of time that the position of first user tool 110 deviates from the target position of first user tool 110 by more than the threshold distance. In some examples, processing circuitry 102 may calculate the performance metric in real-time or in near real-time so that feedback may be provided to the user throughout the respective simulated procedure.

User interface 160 may be configured to generate and present visual information to a user, such as a surgeon, during and/or after the virtual procedure. User interface 160 may include a display (not shown), such as a liquid crystal display (LCD) or a light emitting diode (LED) display or other type of screen, with which processing circuitry 102 may present information related to system 100 (e.g., a visual representation of the position of first user tool 110 within the enclosed space that is bounded by the wall of operation envelope 130). In some examples, user interface 160 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 102 and provide input. In other examples, user interface 160 also includes audio circuitry for providing audible notifications, instructions or other sounds to the user, receiving voice commands from the user, or both. Memory 104 may include instructions for operating user interface 160.

User interface 160 may include any one or more of a mixed reality (MR) display, a virtual reality (VR) display and an augmented reality (AR) display. For example, systems, devices, and methods may employ an MR visualization system to assist with creation, implementation, performance and/or modification of a simulated procedure, such as those simulated procedures which may assist a clinician in gaining skills for performing respective authentic procedures corresponding to the simulated procedures. Because MR, and in some instances VR and/or AR, may be used as a part of simulated procedures described herein, this disclosure may also refer to the simulated procedure as a "virtual" simulated procedure. Visualization tools other than or in addition to mixed reality visualization systems may be used in accordance with techniques of this disclosure. In some examples, system 100 may include one or more cameras configured to track the positions of the user tool during the procedure. When using cameras to track the position of the user tool, system 100 may simulate what obstructions may come into play during the procedure that may limit the ability of the cameras to monitor the movements of the user tool. In this manner, system 100 may identify camera placement issues, and possible corrective actions, that can be made to enable system 100 to visually track the user tool during the simulated procedure and the eventual real procedure on the patient.

In some examples, subsequent to receiving information indicative of the position of the user tool within the enclosed space (or position of the user tool with respect to the enclosed space or virtual boundary) processing circuitry 102 is configured to generate image data for creating an image that renders first user tool 110 in relation to operation envelope 130. Subsequently, processing circuitry 102 may output, to user interface 160, the image data. User interface 160 may be configured to apply the image data in order to display the image. In some cases, the image depicts a virtual representation of a surgical tool inserted into a joint area of a human patient. For example, the image may resemble an x-ray of the joint area that the user would view during an authentic surgical procedure corresponding to the simulated surgical procedure that the user is performing using system 100. In another example, the image may show a perspective view of the anatomy of interest, such as showing bone, muscle, and/or other connective tissue with the skin removed. In any case, processing circuitry 102 may update the image data as first user tool 110 moves within the enclosed space bounded by the wall of operation envelope 130 so that user interface 160 may provide the user real-time or near real-time visual feedback during the simulated medical procedure.

In some examples, user interface 160 is configured to display an image including a path for first user tool 110 to follow in order to complete a simulated procedure. The intended path may include one or more lines (e.g., any one or combination of solid lines, dotted lines, and colored lines) which indicate the path for first user tool 110 to follow through virtual anatomy also displayed in user interface 160. In some examples, the path displayed on user interface 160 may change as first user tool 110 proceeds through the simulated procedure. For example, parts of the path displayed by user interface 160 may disappear as first user tool 110 completes parts of the simulated procedure corresponding to the parts of the path which disappear. In some examples, user interface 160 may display one or more markers indicating, in relation to virtual anatomy, where the first user tool 110 deviated from a target position of first user tool 110 by greater than a threshold amount. In some examples, user interface 160 may display the one or more markers in a different color than user interface 160 displays the path to be followed by first user tool 110. In some examples, system 100 may create a 3D volume of the virtual anatomy for displaying the changes and/or positions of user tool 110 through the process of the simulation. System 100 can then compare the volume created by the user to the ideal volume of the tissue. System 100 can be configured to determine and display whether the user volume is more or less than the target.

In some examples, system 100 may allow a performance of a simulated procedure which includes a set of steps. Each step of the set of steps may include a path for first user tool 110 to follow in relation to virtual anatomy, such as a virtual joint. In some examples, user interface 160 may display the path corresponding to a current step for first user tool 110 to follow in order to complete a simulation procedure. Additionally, in some cases, user interface 160 may be configured to display a path corresponding to a step preceding the current step and/or a path corresponding to a step following the current step. In some examples, user interface 160 may receive user input to switch between displaying paths corresponding to different steps of the set of steps.

In some examples, processing circuitry 102 may control second input device 150 to perform any action described herein as being performed by first input device 140. For example, processing circuitry 102 may control second input device 150 to apply haptic feedback to second user tool 120. In some examples, a simulated procedure may call for a movement of one or both of first user tool 110 and second user tool 120 within operation envelope 130, and user interface 160 may display the movement of one or both of first user tool 110 and second user tool 120 in relation to virtual anatomy such as a virtual joint. In some examples, one or more haptic devices associated with first input device 140 may apply haptic feedback to first user tool 110 and one or more haptic devices associated with second input device 150 may apply haptic feedback to second user tool 120 during a performance of a simulated procedure. In some examples a clinician may control one or both of first user tool 110 and second user tool 120 during a performance of a simulated procedure.

In some examples, user interface 160 may display a position of first user tool 110 and a position of second user tool 120 in relation to virtual anatomy. As such, user interface 160 may display a position of first user tool 110 in relation to second user tool 120. In some examples, the user interface 160 may be configured to receive a user input, such as pulling a trigger or pressing a button on the user tool, to show where the user tool should be during the procedure.

Second user tool 120 may perform any of the techniques described herein as being performed by first user tool 110. Second input device 150 may perform any of the techniques described herein as being performed by first input device 140. In some examples, one or more electrical connections may exist between second user tool 120 and other components of system 100, such as operation envelope 130. In some examples, no electrical connections exist between second user tool 120 and other components of system 100.

In some examples, system 100 may include an anatomic model (e.g., operation envelope 130) with simulated rubber skin/tissue and rigid bone materials pre-cut in one or more osteotomy paths. The one or more osteotomy paths may allow the user of system 100 to develop muscle memory for performing an authentic surgical procedure corresponding to the simulated surgical procedure, in some cases, without haptic feedback. In other words, the anatomical model may be placed within the operation envelope to physically prevent the tool from moving beyond the boundaries of the procedure because the tool contacts the surface of the anatomical model. In some examples, system 100 may identify one or more markers or other landmarks on the anatomical model and register the anatomical model to the operation envelope so that system 100 can track the location of the user tool during the procedure. In addition, or alternatively, system 100 may register the position of the user tool, position of the tool center point, position of an edge or surface of the tool (e.g., for a saw, router, or other cutting bit), orientation of the user tool or portion of the user tool, the direction in which the user tool is pointing (e.g., line vector, or planar vector), or any other aspect of the user tool, with respect to the operation envelope, one or more sensors, the anatomical model, or any other coordinate system used by system 100 to track the movement of the user tool. System 100 may utilize one or more markers added to the user tool and/or one or more landmarks of the user tool and identifiable by system 100. In some cases, system 100 may use haptic feedback to alert the user to mistakes made in the simulated surgical procedure. Operation envelope 130 may allow the user to operate first user tool 110 and/or second user tool 120 much like a gear shift or a stencil when first user tool 110 and/or second user tool 120 is inserted into the one or more apertures of operation envelope 130. In this way, user tools 110, 120 may not need to actually cut any material, but rather follow pre-cut planes, enabling the user to develop muscle memory for the movements required for the procedure. User interface 160 may display a virtual view (e.g., anatomical structures beneath the skin) during the simulated surgical procedure by displaying quadrant cutting techniques.

Additionally, a combination of haptics registered with a simulated foot (with rigid boundaries) can replicate the constraints found when a surgeon applies a key-hole surgical approach during an authentic surgical procedure. For example, operation envelope 130 may include a plurality of potential entry points, such as the one or more apertures formed in the wall of operation envelope 130. This may be beneficial for mimicking the surgical case where the surgeon determines the entry point of the burr. In other words, by including several apertures, or entry points, the surgeon may be given more options for performing the simulated surgical procedure as the surgeon would perform a corresponding authentic surgical procedure. Processing circuitry 102 could factor the user's choice of entry point (e.g., choice of aperture) into a grading system to give the surgeon feedback as to an ability to avoid neurovascular structures and remain within "safe zones" during the simulated surgical procedure. For an application where pivoting resistance is not practical (additional degrees of freedom), a rigid model such as operation envelope 130 may simulate boundaries in the same way disclosed burr guides restrain motion out of plane. In some examples, operation envelope 130 may be subdermal and re-usable.

System 100 may be applied in various surgical applications and procedures, such as Minimally Invasive Chevron and Akin (MICA™) Osteotomy, Calcaneal Osteotomy, or Distal Metatarsal Minimal Invasive Osteotomy (DMMO). In some examples, one or both of input devices 140, 150 may interface with an MR trainer, a VR trainer, an AR trainer, or any combination thereof. In some examples, system 100 may include one or more of an MR display, a VR display, and an AR display for displaying at least one surgical procedure.

In some examples, processing circuitry 102 may function as a game-like simulator and track a record performance metric among one or more users. For example, the one or more users may each perform a simulated procedure using system 100. Processing circuitry may generate a performance metric corresponding to each user of the one or more users based on a performance level of each respective user. The performance metric may be affected by an amount of time that first user tool 110 and/or second user tool 120 deviates from a target position of first user tool 110 and/or second user tool 120. For example in a first simulated procedure corresponding to a first user, a position of first user tool 110 may deviate from a target position of first user tool 110 for a first amount of time, and in a second simulated procedure corresponding to a second user, a position of first user tool 110 may deviate from a target position of first user tool 110 for a second amount of time, where the second amount of time is longer than the first amount of time. Processing circuitry 102 may dock a lower number of points from the performance metric corresponding to the first simulated procedure than the performance metric corresponding to the first simulated procedure for total time deviated, since first user tool 110 deviated from the target position for a greater amount of time in the second simulated procedure. Additionally, or alternatively, in some cases, processing circuitry 102 may calculate the performance metric based on a total amount of time to complete the simulated procedure, a total amount of distance that user tool 110 deviates from the target position throughout the procedure, a number of steps successfully completed, or any combination thereof.

In some examples, processing circuitry 102 may output data indicative of a list of performance metrics for display by user interface 160, where each performance metric of the list of performance metrics is associated with a particular user. User interface 160 may receive an input to share a performance metric on a social media account or post the performance metric to an email. Additionally, in some cases, processing circuitry 102 may output a list of contact information corresponding to the users associated with the list of performance metrics. In some examples, processing circuitry 102 may select the list of performance metrics for outputting to user interface 160 based on an identity of a current user of system 100. For example, processing circuitry 102 may output performance metrics of users that are employed by the same clinic as the current user of system 100. Additionally, or alternatively, processing circuitry 102 may output performance metrics of users that have the same number of years of professional experience of the current user of system 100.

Processing circuitry 102 may also employ artificial intelligence in the form of one or more types of machine learning to provide various outputs related to the simulation environment. Processing circuitry 102 may employ one or more machine learning algorithms, which may include supervised algorithms, when performing one or more tasks integrated with simulation system 100. Some such machine learning algorithms are described in an article entitled "Topics in Training" by Bissonnette et al., published in the Journal of Bone and Joint Surgery in Volume 101-A, Number 23, on Dec. 4, 2019, which is referenced herein in its entirety. Applicable supervised algorithms include but are not limited to support vector machine learning, linear discriminant analysis, k-nearest neighbors, Naïve Bayes, and decision tree.

Processing circuitry 102 may be configured to acquire data such as various inputs, process with inputs the one or more artificial intelligence methodologies, and output one or more performance metrics. These steps include but are not limited to receiving raw data, metric extraction, metric normalization, metric selection, machine learning algorithms, and model selection. Received raw data information may include but is not limited to position of simulated anatomy, user tool position, angles, speeds, accelerations, and resistance forces generated by one or more sensors included in, or in communication with, system 100.

In an additional application of (AI) artificial intelligence, the AI can compare a user's performance metrics with a "physical guidance" to a "non-physical guidance" or "freehand" scenario. Once the user has logged a sufficient number of samples (n=1 or more), processing circuitry 102 can, using the AI algorithms, suggest areas of improvement with pattern recognition and statistical relevance. As described herein, processing circuitry 102 may be configured to measure the virtual cut made with a bone burr (e.g., a cutting tool) when freehand and output a warning notification in a real-time simulation which can pause the simulation and alert the user when and where the burr is not cutting in the desired path. The AI alert generated by processing circuitry 102 may be configured to pause the simulation and communicate the error to be avoided in context of the procedure. In the example of a bone burr cutting out of plane, processing circuitry 102 may pause the simulation to alert the user and request correction of the user tool until it is in the desired position. In this scenario, processing circuitry 102 may employ the AI algorithm to compare the user's freehand performance to a physically guided simulation.

Additionally, processing circuitry 102 may compare the user's freehand metrics to freehand metrics of other users targeting a "perfect bone cut pattern" (e.g., a target pattern of bone cut for the procedure) and measuring accuracy and reproducibility. It is understood that the physical guidance scenario allows for a range of positional tolerance. Processing circuitry may also employ these AI algorithms to analyze the performance of multiple samples and users to provide a data set which can be used and shared amongst users, manufacturers, or any other entities. This data set can output a user's simulated surgical metrics and compare to both metrics of multiple users in addition to the "perfect bone cut pattern" with a statistical probability. Metrics are analyzed by the machine learning algorithm employed by processing circuitry 102 and output in categories including but not limited to safety, efficiency, coordination, motion of tools, virtual bone temperatures, and comparative reproducibility with and without physical guidance.

There can be levels/grades of challenge with haptic assistance turned on and off. Beginner levels may include full robotic control of position while advanced levels allow cutting outside virtual boundaries including tracking of accuracy around specific obstacles/anatomy. User interface 160 may display simulated x-ray vision generated from the computer model as well as projected planes and angles to aid training. Augmented vision (i.e., augmented reality) may highlight presence/location of neurovascular structures to familiarize user with "safe zones" or "keep out zones" and general anatomy.

In some examples, processing circuitry 102 may output data indicative of feedback from a third-party user. Processing circuitry 102 may output the feedback to, for example, user interface 160. The third-party user, in some cases, may represent a remote trainer. The remote trainer may interact with a remote device which is configured to receive user input indicative of one or more aspects of a simulated procedure. For example, the remote device may receive data indicative of one or both of first user tool 110 and second user tool 120 in relation to a virtual joint. The user device may receive data indicative of a path of one or both of first user tool 110 and second user tool 120 in relation to a virtual joint. The data may include information relating to one or more instances in which one or both of first user tool 110 and second user tool 120 deviates from a target position by more than a threshold amount. Processing circuitry 102 may receive feedback indicative of one or more suggestions, tips, a performance metric, or any combination thereof. The data indicative of the feedback may include any one or combination of audio feedback (e.g., beeping, talking, tool sounds, etc.), visual feedback (e.g., lights, images, direction arrows, etc.), and haptic feedback (e.g., vibration, tool force changes, etc.). The remote device may send the data indicative of the feedback to processing circuitry 102 in real-time or near real-time.

In some examples, system 100 may be configured to function as a planning tool to aid communication and reproducibility by means of software. For example, processing circuitry 102 may allow simulation modalities with varied levels of challenge including providing guidance by input devices 140, 150 in a correct cutting plane, activating and deactivating free hand cutting (e.g., without guidance by input devices 140, 150). Additionally, processing circuitry 102 may allow one or more simulation modalities involving user interface 160, such as and displaying a target plane or line for operation using user interface 160 and obscuring view of bones beneath skin, displaying a line of sight. Additionally, processing circuitry 102 may add anatomic targets and obstacles, simulate interruptions like a broken burr or vitals check, provide non-anatomic examples for virtual practice generate soft bumpers or beeping to indicate when a position of one or both of user tools 110, 120 is outside of a desired plane, and simulate drilling, insertion of screws, and any other common orthopedic steps. Additionally, processing circuitry 102 may track performance metrics, including a time required to complete a procedure, predicted heat generation peaks (e.g., avoiding tissue necrosis), accuracy, and an amount (e.g., volume) of bone removed. In some examples, results of the simulated procedure, or portions there, may be used by the clinician to generate or modify a surgical procedure plan. For example, the clinician can identify desired paths of the tool, volumes of tissue to be removed, tool angles, motions, procedure orders, etc. for the planned procedure. The clinician may desire to use different angles due to right or left handedness or variation on patient anatomy. Processing circuitry 102 may then port the requested changes to the procedure plan to a surgical system or other device that facilitates the patient's procedure. In some examples, processing circuitry 102 may simulate the procedure using the clinician's procedure plan generated for a specific patient. In this manner, the user can directly request changes to the procedure plan based on the simulation using system 100. These and other techniques for procedure planning are described in U.S. patent application publication no. 2019/0142520 by VanDyken and filed on Nov. 12, 2018, the entire contents of which are incorporated herein by reference.

Processing circuitry 102 may predict an amount of heat that one or both of first user tool 110 and second user tool 112 generates during a simulated procedure. In some examples processing circuitry 102 may predict the amount of mead based on any one or combination of a set of factors including an amount of rotations per minute (RPMs) of the respective user tool, a movement speed of the respective user tool, and a flow rate of saline into an area proximate to the respective tool. For example, higher RPMS, slower movement speed, and lower flow rate of saline may result in higher heat generation and higher temperatures in tissue surrounding the user tool 112. In some examples, the target position of a user tool may depend on the predicted amount of heat. For example, the target opposition of the user tool may change in order to avoid heat buildup in a particular location.

FIG. 2 is a schematic diagram illustrating a system 200, which is an example of the system 100 of FIG. 1, in accordance with one or more techniques of this disclosure. As illustrated in FIG. 2, system 200 includes first user tool 210, second user tool 220, operation envelope 230, first input device 240, second input device 250, and user interface 260. Apertures 232A-232E (hereinafter, "apertures 232") may be formed in operation envelope 230. First user tool 210 may be an example of first user tool 110 of FIG. 1. Second user tool 220 may be an example of second user tool 120 of FIG. 1. Operation envelope 230 may be an example of operation envelope 130 of FIG. 1. First input device 240 may be an example of first input device 140 of FIG. 1. Second input device 250 may be an example of second input device 150 of FIG. 1. User interface 260 may be an example of user interface 160 of FIG. 1.

User 201 may perform a simulated surgical procedure using system 200. For example, as illustrated in FIG. 2, user 201 may handle first user tool 210 and second user tool 220, where first user tool 210 is received by aperture 232A and second user tool 220 is received by aperture 232B. In some examples not illustrated in FIG. 2, user 201 may handle only none, or only one of first user tool 210 and second user tool 220. Additionally, in some examples not illustrated in FIG. 2, each of first user tool 210 and second user tool 220 may be received by any one of apertures 232 or by none of apertures 232, depending on the simulated surgical procedure being performed using system 200. In some cases, user 201 may perform the simulated procedure while receiving haptic feedback from first input device 240 and/or second input device 250 and receiving visual feedback form user interface 260. System 200 may perform any one or more of the techniques described with respect to system 100 of FIG. 1.

Figure 3:
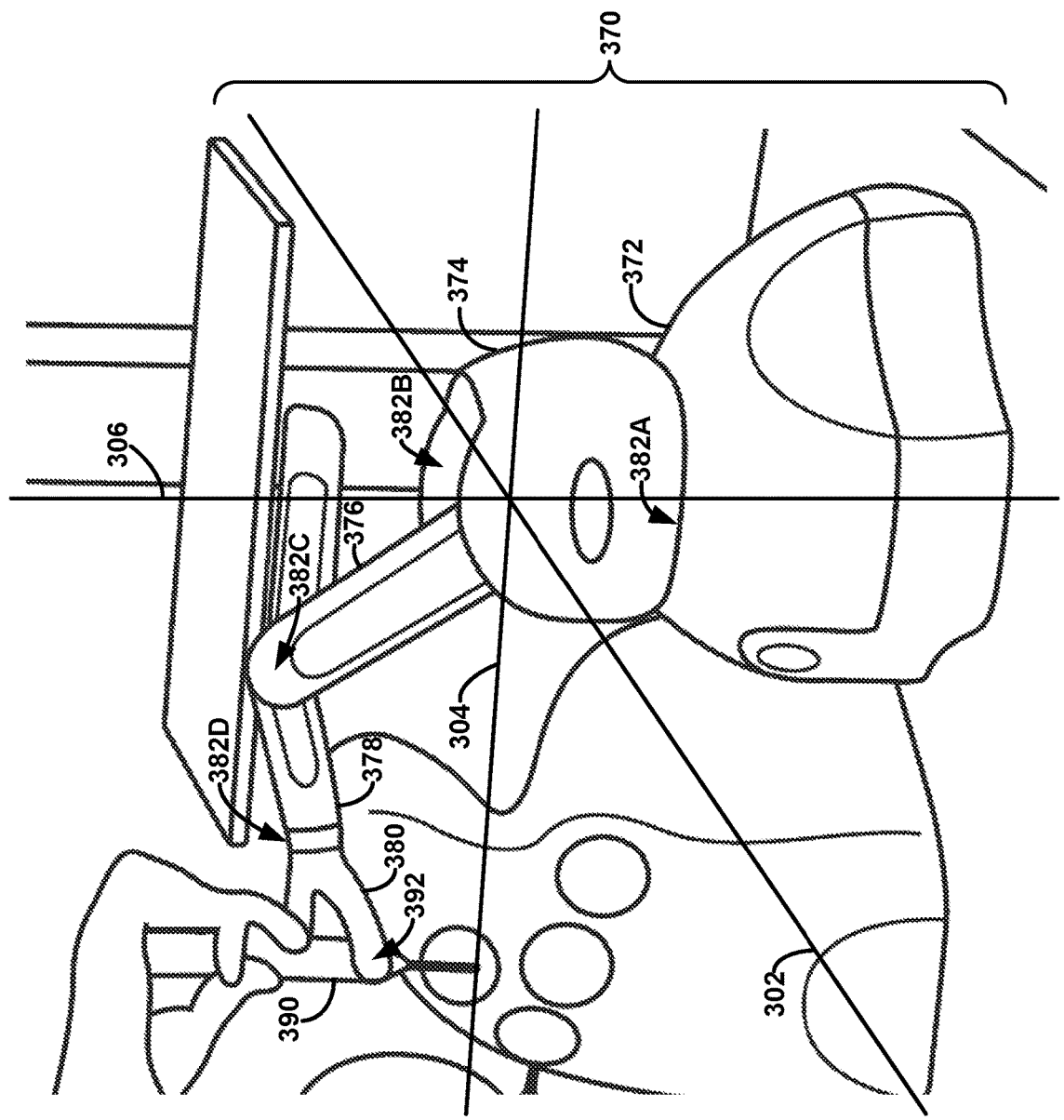
FIG. 3 is a schematic diagram illustrating an input device mechanically connected to a user tool, in accordance with one or more techniques of this disclosure.

FIG. 3 is a schematic diagram illustrating an input device 370 mechanically connected to a user tool 390, in accordance with one or more techniques of this disclosure. In some examples, input device 370 may be an example of first input device 140 of FIG. 1. In some examples, input device 370 may be an example of second input device 150 of FIG. 1. In some examples, user tool 390 may be an example of first user tool 110 of FIG. 1. In some examples, user tool 390 may be an example of second user tool 120 of FIG. 1. As illustrated in FIG. 3, input device 370 includes first base section 372, second base section 374, first arm 376, second arm 378, and fork section 380. Additionally, input device 370 includes joints 382A-382D (collectively, "joints 382").

Input device 370 may perform any one or more of the techniques that may be performed using first input device 140 of FIG. 1, second input device 150 of FIG. 1, first input device 240 of FIG. 2, and second input device 250 of FIG. 2. For example, input device 370 may be mechanically connected to user tool 390 at joint 392. A user may handle user tool 390 during a simulated surgical procedure, and input device 370 may apply or refrain from applying a mechanical force to user tool 390 based a set of control parameters. Input device 370 may receive the set of control parameters from processing circuitry (e.g., processing circuitry 102 of FIG. 1, where the processing circuitry generates the set of control parameters based on a position of user tool 390 in relation to an operation envelope (e.g., operation envelope 130 of FIG. 1). For example, if user tool 390 deviates from a target position in relation to the operation envelope, the processing circuitry may generate the set of control parameters to cause input device 370 to guide user tool 390 towards the target position. Additionally, or alternatively, the processing circuitry may generate the set of control parameters to cause input device 370 to apply a mechanical stimulus to user tool 390, the mechanical stimulus indicating to the user that user tool 390 is separated from the target position.

Input device 370 may be configured to apply pressure to user tool 390. In the example of FIG. 3. Although depicted as a static device in FIG. 3, input device 370 may be configured to move within a three-dimensional space defined by x-axis 302, y-axis 304, and z-axis 306. In the example illustrated in FIG. 3, x-axis 302 is orthogonal to y-axis 304. Additionally, z-axis 306 is orthogonal to both x-axis 302 and y-axis 304. In some examples, a coordinate system which defines the three-dimensional space may include one or more of a cartesian coordinate system, a polar coordinate system, a spherical coordinate system, and a spherical coordinate system. Although input device 370 is illustrated as including first base section 372, second base section 374, first arm 376, second arm 378, and fork section 380, In some examples not illustrated in FIG. 3, input device 370 may include a base that is configured to move in two dimensions (e.g., x-axis 302 and y-axis 304) and a section that is configured to move in a third dimension (e.g., z-axis 306).

In some examples, each joint of joints 382 may include one or more electric motors and one or more sensors. These motors and sensors may be in addition to, or alternative from, fixed or adjustable physical stops associated with each of joints 382. For example, an electric motor may control movement at a respective joint of joints 382 and a sensor may sense a position of the respective joint of joints 382. In some examples the electric motors which control movement at joints 382 may be referred to as "haptic devices," since the electric motors which control movement at joints 382 in turn cause a movement of input device 370 in order to apply pressure to user tool 390.

First base section 372 may rest on a floor, a table, or another surface configured to support input device 370. Second base section 374 rests on first base section 372.

Additionally, second base section 374 may rotate relative to first base section 372 about an axis passing through a center of first base section 372, the axis being parallel to z-axis 306. The rotation of first base section 372 relative to second base section 374 may be controlled by one or more electrical motors. The set of control parameters generated by the processing circuitry may cause the one or more electrical motors to rotate, thus causing first base section 372 to rotate relative to second base section 374. In some examples, second base section 374 may be configured to rotate at least 180 degrees relative to first base section 372. In some examples, second base section 374 may be configured to rotate at least 360 degrees relative to first base section 372.

In some examples, first arm 376 is mechanically connected to second base section 374 at joint 382B. In the example illustrated in FIG. 3, joint 382B may be obscured within second base section 374. First arm 376 may rotate relative to second base section 374 by rotating about an axis that passes through joint 382B. In some cases, the axis that passes through joint 382B is orthogonal to z-axis 306. Joint 382B rotates relative to first base section 372 along with second base section 374. As such, the axis which passes through first base section 372 rotates but remains within a plane that includes x-axis 302 and y-axis 304. One or more electrical motors may control the rotation of first arm 376 about the axis that passes through joint 382B based on the set of control parameters generated by the processing circuitry. In some examples, first arm 376 may be configured to rotate at least 180 degrees about the axis that passes through joint 382B. In some examples, second arm 378 is mechanically connected to first arm 376 at joint 382C. Second arm 378 may rotate relative to first arm 376 about an axis that passes through joint 382C, where the axis that passes through joint 382C is perpendicular to z-axis 306. One or more electrical motors may control the rotation of second arm 378 relative to first arm 376. Fork section 380 may rotate relative to second arm 378 at joint 382D. Fork section 380 may rotate about an axis that passes through second arm 378, the axis being parallel to second arm 378. In this way, fork section 380 may "twist" relative to second arm 378. One or more electric motors may control the rotation of fork section 380 relative to second arm 378.

Since input device 370 is mechanically connected to user tool 390 at joint 392, and electrical motors may control components (e.g., first base section 372, second base section 374, first arm 376, second arm 378, and fork section 380) to move relative to each other. In this way, input device 370 may be configured to apply pressure to user tool 390 in order to cause user tool 390 to move and/or apply a mechanical stimulus (e.g., mechanical vibration or mechanical pulsing) to user tool 390.

Figure 4:
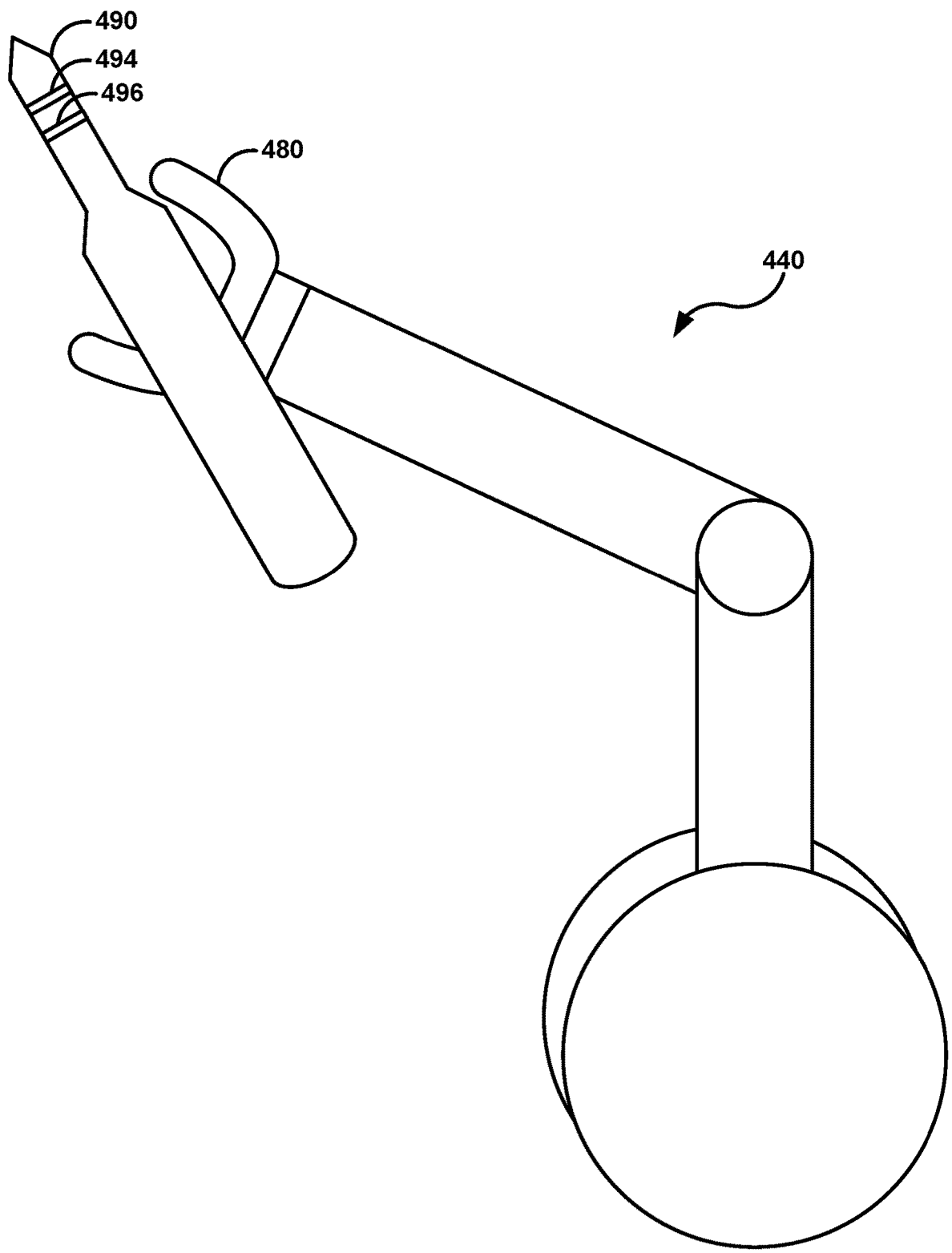
FIG. 4 is a conceptual diagram illustrating a robotic arm configured to grip a surgical tool, in accordance with one or more techniques of this disclosure.

FIG. 4 is a conceptual diagram illustrating a robotic arm 440 configured to grip a surgical tool 490, in accordance with one or more techniques of this disclosure. Robotic arm 440 may be an example of any one of first input tool 140 and second input tool 150 of FIG. 1. Robotic arm 440 may include grip 480 which is configured to secure surgical tool 490 to robotic arm 440. In some examples, robotic arm 440 may be configured to apply pressure to surgical tool 490 in the form of haptic feedback during a simulated surgical procedure. For example, surgical tool 490 may be configured to move within a space formed by an operation envelope. Processing circuitry (e.g., processing circuitry 102 of FIG. 1) may be configured to determine a position of surgical tool 490 within the operation envelope based on determining a position of marker 494 and marker 496. For example, the processing circuitry may receive data indicative of a position of marker 494 and a position of marker 496 and determine a depth and/or an angle of surgical tool 490 based on the position of marker 494 and the position of marker 496. In some examples, surgical tool 490 may represent a drill, a stylus, a scalpel, saw, cautery, laser, or another type of surgical tool. In some examples, depending on the type of tool, the system may track a location away from the tool itself that would be associated with the cutting area from the tool (e.g., the impact from a laser cutting tool that occurs a physical distance away from the tool itself). In some examples, the system may track a swing of a blade or even heat caused by use of the tool during the simulated procedure.

Figure 5:
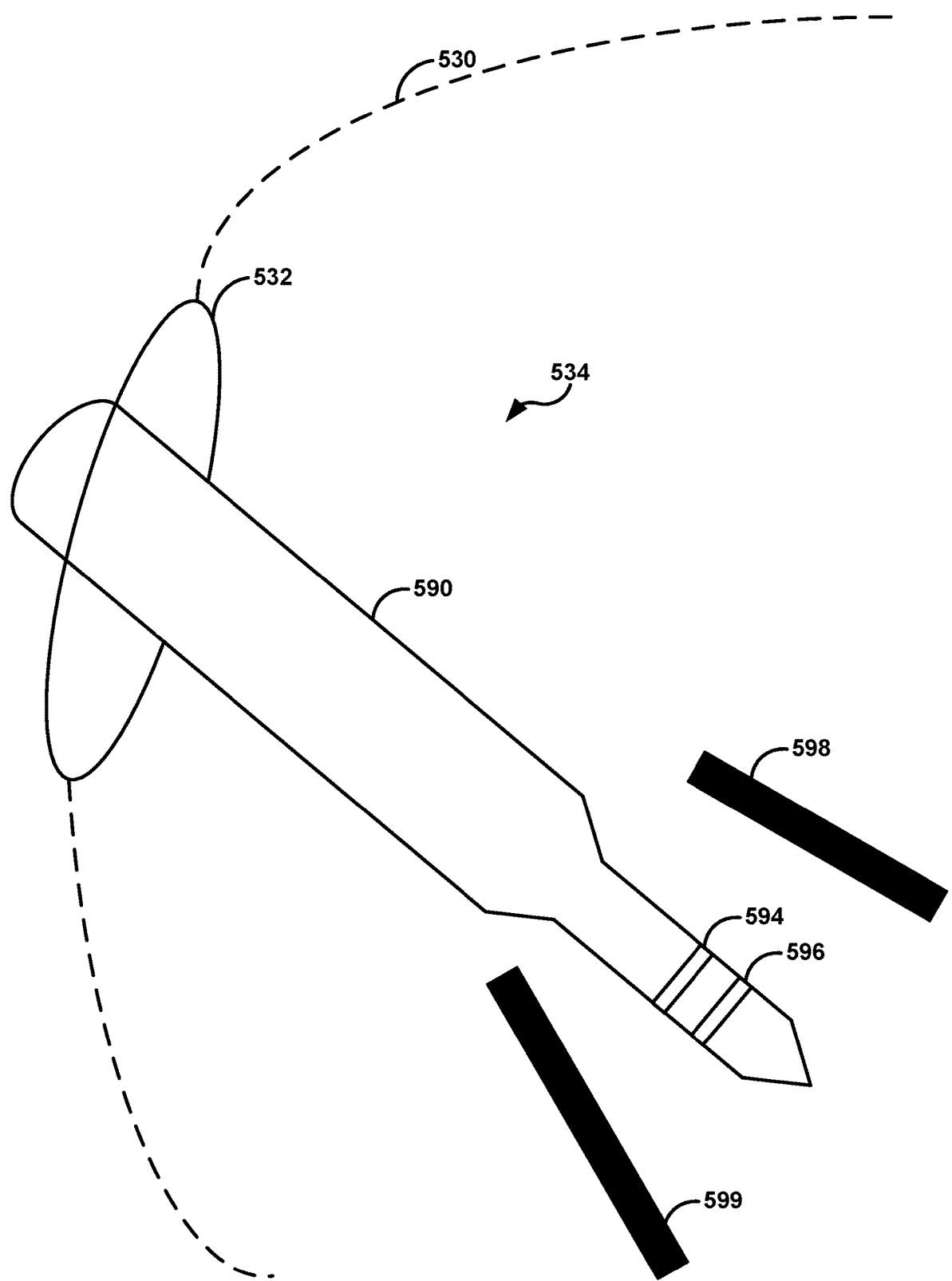
FIG. 5 is a conceptual diagram illustrating a user tool within or relative to an operation envelope, in accordance with one or more techniques of this disclosure.

FIG. 5 is a conceptual diagram illustrating a user tool 590 within an operation envelope 530, in accordance with one or more techniques of this disclosure. In some examples, user tool 590 may be an example of any one of first user tool 110 and second user tool 120 of FIG. 1. Operation envelope 530 may be an example of operation envelope 130 of FIG. 1. User tool 590 may be configured to engage with operation envelope 530 through aperture 532 which is formed through a sidewall of operation envelope 530. Operation envelope 530 may form a space 534 in which user tool 590 is configured to move. Physical guide 598 and physical guide 599 may be placed within the space 534 in order to limit a movement of user tool 590 within operation envelope 530. Physical guide 598 and physical guide 599 may be placed in space 534 according to one or more simulated procedures to be performed using operation envelope 530. In other examples, only one physical guide, or more than two physical guides, may be placed within operation envelope 530. Physical guides 598 and 599 may be configured to attach to or be placed against a wall of operation envelope 530. Physical guides 598 and 599 may be configured to be placed on a surface within operation envelope 530. In some examples, physical guides 598 and 599 may be electrically coupled to system 100 such that the system can detect when user tool 590 contacts one of physical guides 598 and 599.

Figure 6:
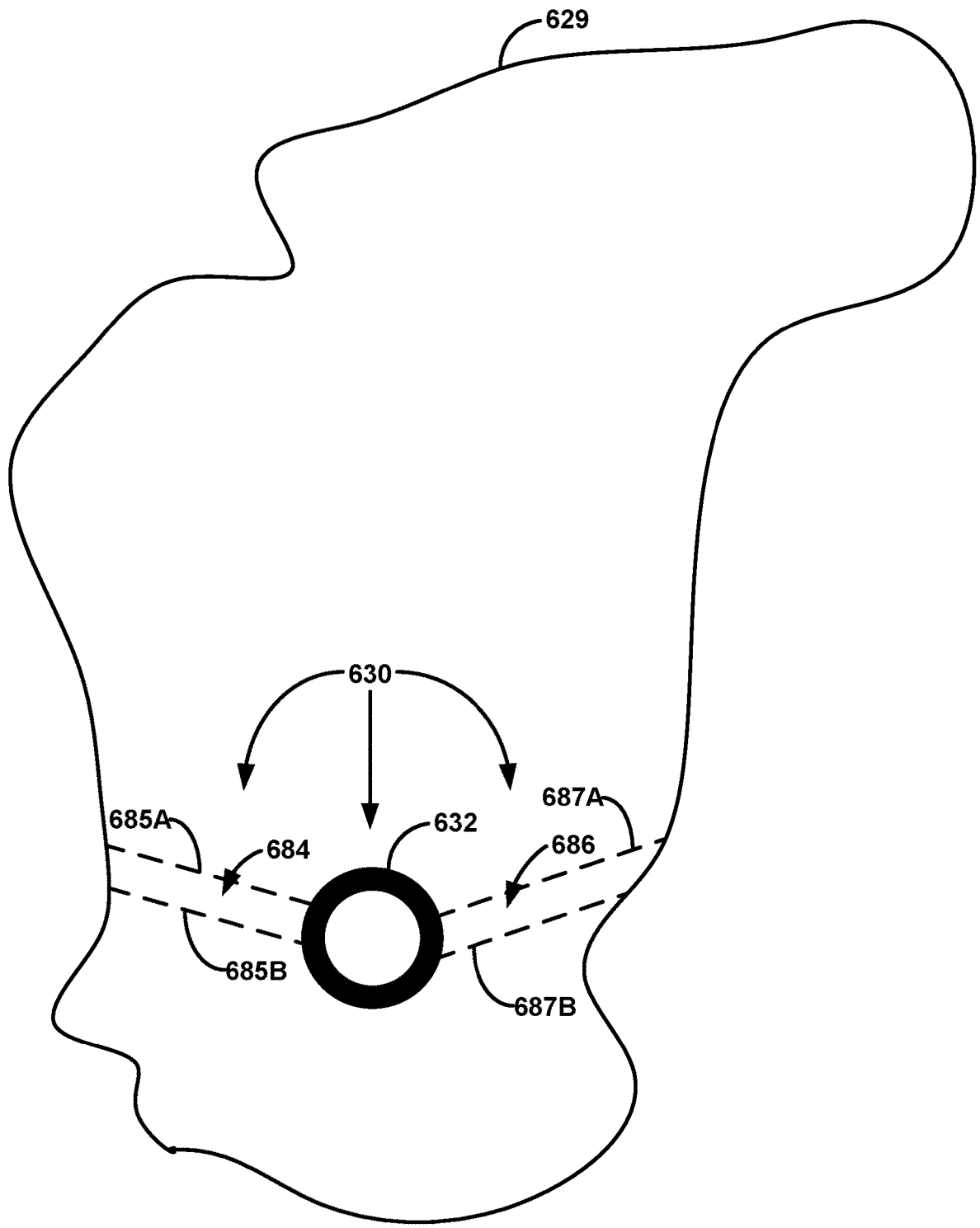
FIG. 6 is a conceptual diagram illustrating a top view of a simulation device which forms an operation envelope, in accordance with one or more techniques of this disclosure.

FIG. 6 is a conceptual diagram illustrating a top view of a simulation device 629 which forms operation envelope 630, in accordance with one or more techniques of this disclosure. As seen in FIG. 6, operation envelope 630 may include aperture 632, first channel 684, and second channel 686 (collectively, "channels 684, 686") defined by the structure of simulation device 629. In some examples, aperture 632 may be configured to receive a user tool which represents a surgical tool for performing a simulated medical procedure. In some examples, aperture 632 may receive one or both of first user tool 110 and second user tool 120 of FIG. 1. In some examples, simulation device 629 may represent one or more bones of a human joint (e.g., a knee, an ankle, a wrist, or an elbow), and channels 684, 686 may represent a target cut to be made during a real-life medical procedure in which the simulated medical procedure is designed to mimic. For example, if simulation device 629 is a model of an ankle, a location of aperture 632 on simulation device 629 may correspond to a point on a human ankle in which it is beneficial to insert a surgical tool during the real-live surgical procedure in which the simulated procedure is modeled after. As seen in FIG. 6, channel 684 extends in a first direction and channel 686 extends in a second direction, where the first direction forms an angle with the second direction at aperture 632. In some cases, the angle is within a range from 90 degrees to 180 degrees. When the angle is 180 degrees (not illustrated in FIG. 6), first channel 684 and second channel 686 extend across simulation device 629 in a straight line along a common axis, where aperture 632 is located between first channel 684 and second channel 686.

Simulation device 629 may be constructed from one or more materials such as nylon, polylactic acid (PLA), acrylonitrile butadiene styrene (ABS), or polyethylene terephthalate (PETG), or other kinds of plastics. A three-dimensional (3D) printer may create simulation device 629 in some cases. In some examples, simulation device 629 may be composed of solid material in all areas. In some examples, simulation device 629 may be hollow with the exception of walls that define channel 684 and 686. In some examples, simulation device 629 may represent a wall of material which forms aperture 632 and channels 684, 686. In any case, aperture 632 and channels 684, 686 may enable a user tool to move within operation envelope 630 according to one or more movements of a simulated procedure, such as one or more simulated bone cuts. The material of simulation device 629 may prevent the user tool from moving beyond a boundary of a simulated movement of the simulated procedure. In other words, the material of simulation device 629 may confine the user tool to channels 684, 686 since the user tool might not be configured to pierce, cut, or otherwise degrade the material of Simulation device 629. In this manner, the user may build muscle memory by being forced into the desired cut for the procedure defined by channels 684, 868. First channel 684 may include boundary 685A and boundary 685B. Second channel 686 may include boundary 687A and boundary 687B.

Figure 7:
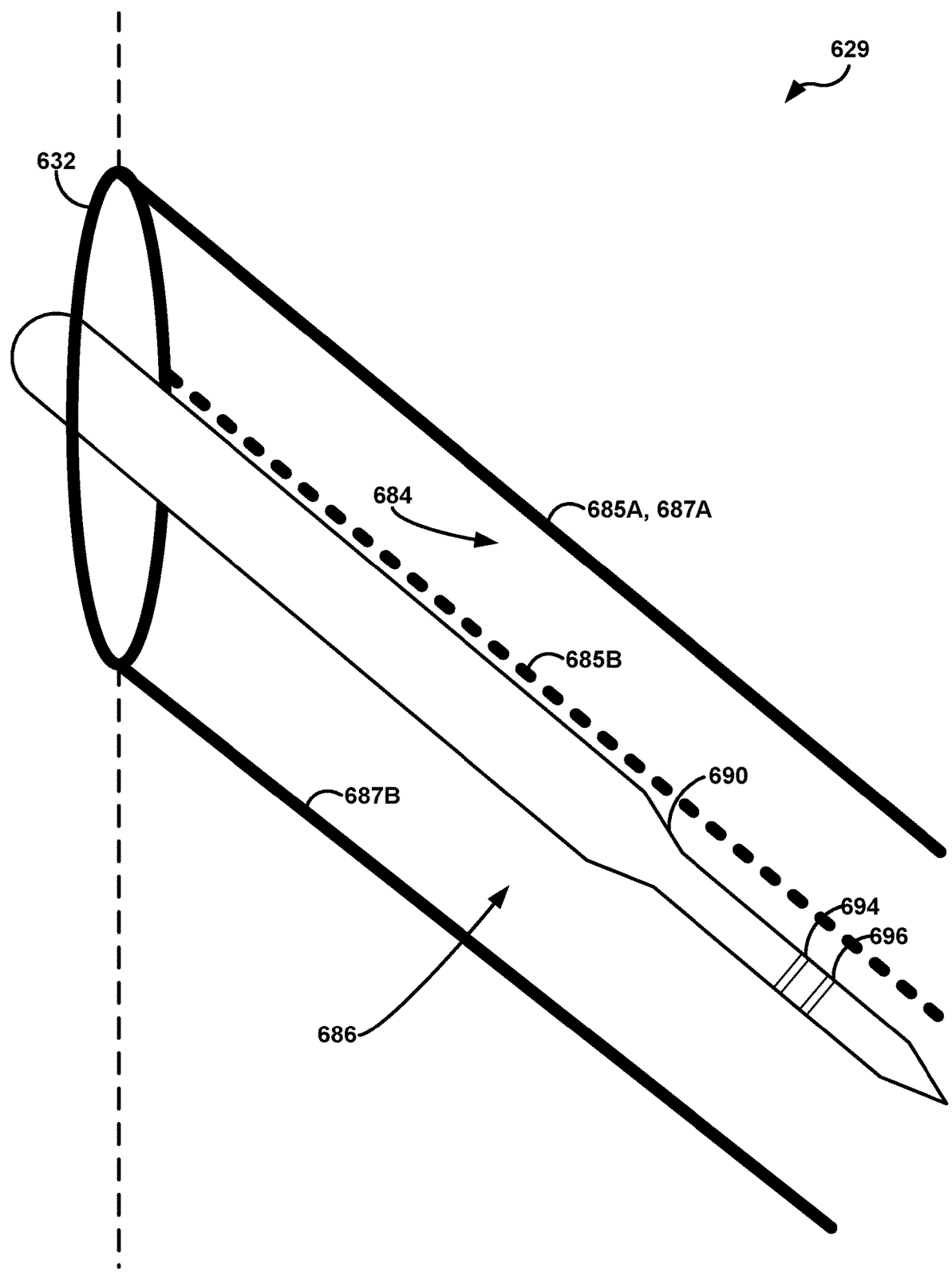
FIG. 7 is a conceptual diagram illustrating a cross-sectional view of a simulation device which forms an operation envelope, in accordance with one or more techniques of this disclosure.

FIG. 7 is a conceptual diagram illustrating a cross-sectional view of a simulation device 629 which forms operation envelope 630, in accordance with one or more techniques of this disclosure. As seen in the example of FIG. 7, operation envelope 630 is configured to receive user tool 690. User tool 690 may be configured to move within an operation envelope (e.g., operation envelope 630 of FIG. 6), which includes first channel 684 and second channel 686. In some examples, second channel 686 may extend directly outward from the page of FIG. 7. For example, boundary 687A and boundary 687B may extend outwards from the page of FIG. 7, thus forming second channel 686. User tool 690 may pivot at aperture 632 and enter second channel 686. Additionally, or alternatively, user tool 690 may pivot at aperture 632 and enter first channel 684 which is bounded by boundary 685A and boundary 685B. In some examples, user tool 690 may include marker 694 and marker 695. Simulation device 629 may include one or more sensors to generate data indicative of a position of user tool 690 within operation envelope 630 based on a position marker 694 and a position of marker 695.

Figure 8:
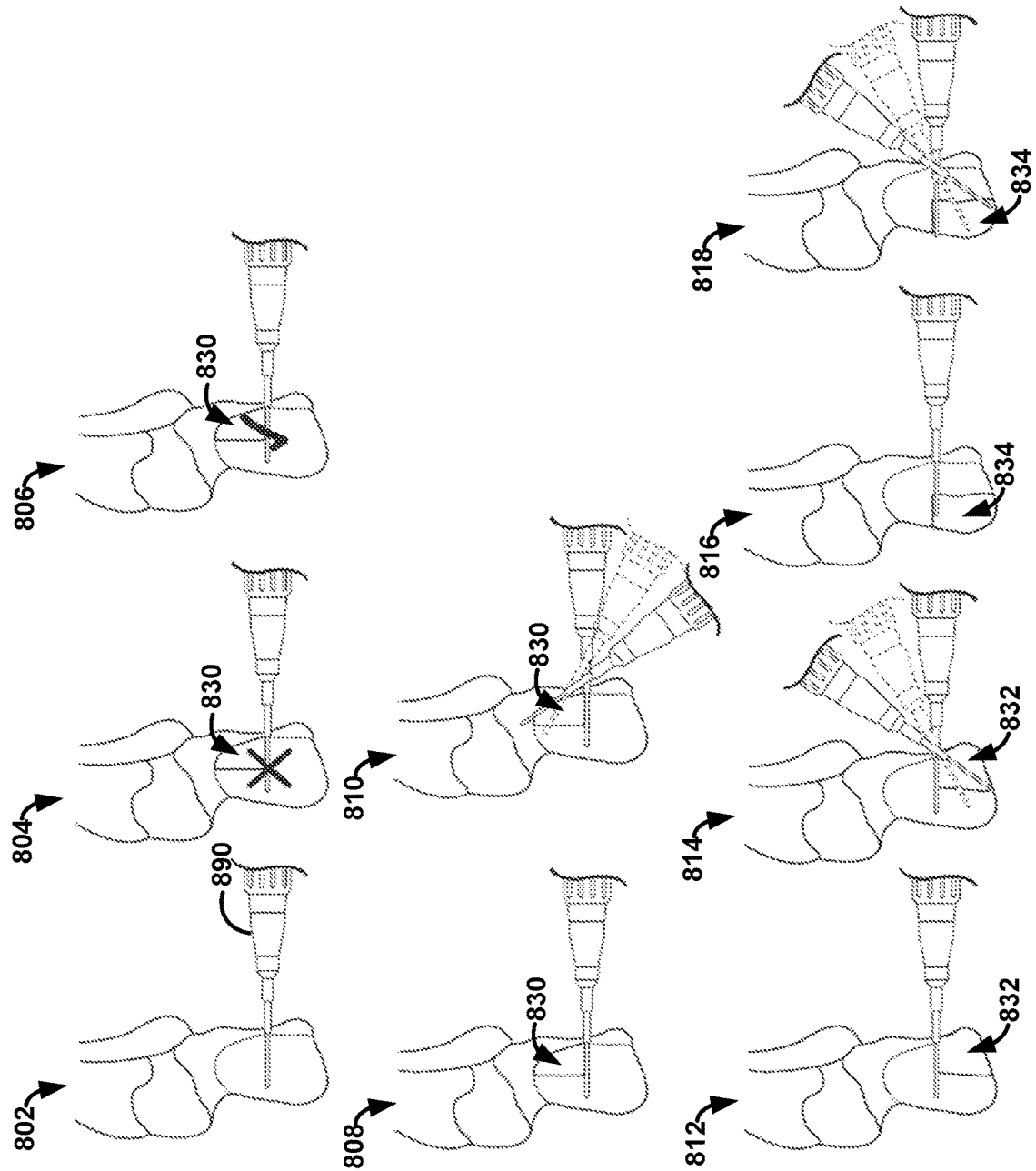
FIG. 8 is a conceptual diagram illustrating a set of steps of a surgical procedure, in accordance with one or more techniques of this disclosure.

FIG. 8 is a conceptual diagram illustrating a set of steps 802-818 of a surgical procedure, in accordance with one or more techniques of this disclosure. For example, steps 802-808 may represent a set of steps of a simulated surgical procedure that is performed using system 100 of FIG. 1.

In some examples, the surgical procedure illustrated by FIG. 8 represents an arthroplasty procedure. Arthroplasty procedures, in some examples, may be performed in order to restore or improve a function of a joint, such as an ankle, a knee, a hip, a wrist, an elbow, or a shoulder. Arthroplasty procedures may involve removing cartilage from a joint area, carving bone in the joint area, and/or placing one or more implants at the joint area. Since skin covers a joint area of a patient, it may be difficult or impossible for a surgeon to see a surgical tool cutting, carving, or implanting at the joint area during the procedure. In this way, it may be beneficial for a surgeon to perform the simulated surgical procedure represented by steps 802-804 so that the surgeon gains skills for performing an authentic surgical procedure corresponding to the simulated surgical procedure.

At step 802, user tool 890 is inserted into an operation envelope (e.g., operation envelope 130 of FIG. 1). A user interface (e.g., user interface 160 of FIG. 1) may display the image seen in FIG. 8 corresponding to step 802. If user tool 890 is inserted too far, or deep, into the operation envelope, the user interface may display the step 804 image which includes an ("X"). If user tool 890 is at a correct position, the user interface may display the step 806 image which includes a check mark, indicating the correct position for the procedure at step 806. Steps 804-810 include a first shaded area 830 representing a simulation of an area of bone to be carved, or removed, using a surgical instrument represented by user tool 890. In step 810, a user may manipulate user tool 890 to mimic carving bone at the first shaded area 830. Additionally, steps 812 and 814 include second shaded area 832 and steps 816 and 818 include third shaded area 834. At step 814, the user may manipulate user tool 890 to mimic carving bone at the second shaded area 832. At step 818, the user may manipulate user tool 890 to mimic carving bone at the third shaded area 834. System 100 may employ boundaries to force and/or track user tool 890 to stay within a threshold distance of a target position of user tool 890. For example, first input device 140 of FIG. 1 may apply a force to user tool 890 to keep user tool 890.

Figure 9:
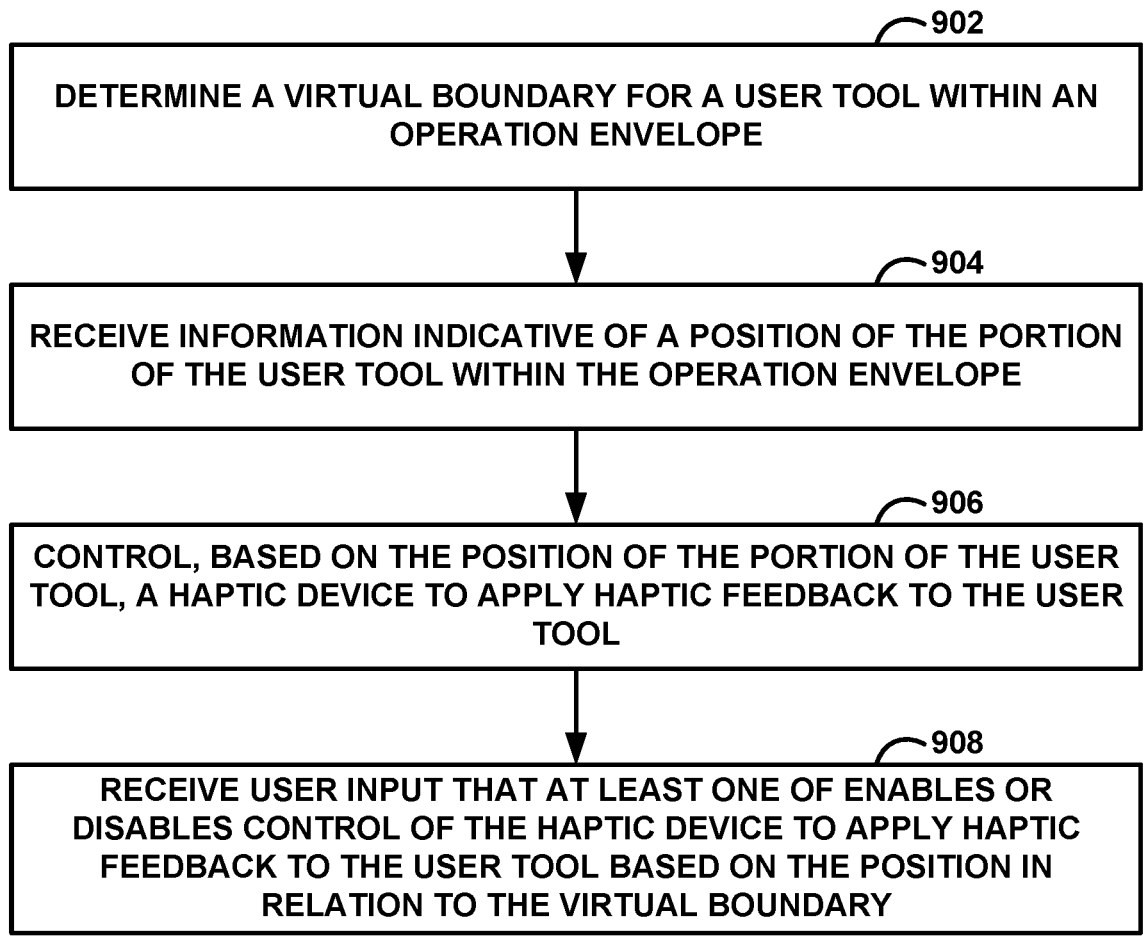
FIG. 9 is a flow diagram illustrating an example operation for performing a simulated surgical procedure, in accordance with one or more techniques of this disclosure.

FIG. 9 is a flow diagram illustrating an example operation for performing a simulated surgical procedure, in accordance with one or more techniques of this disclosure. For convenience, FIG. 9 is described with respect to system 100 of FIG. 1. However, the techniques of FIG. 9 may be performed by different components of system 100 or by additional or alternative medical devices.

In some examples, system 100 may allow a performance of a simulated procedure, where the simulated procedure mimics a real-world medical procedure to be performed on a patient. Such a simulated procedure may include a series of movements of a user tool, such as first user tool 110, the series of movements being similar to a series of movements that are performed during the real-world medical procedure to be performed on the patient. Processing circuitry 102 of system 100 may determine a virtual boundary for user tool 110 within operation envelope 130 (902). The virtual boundary may represent an acceptable range of positions for user tool 110 to occupy within operation envelope 130. For example, a target position may be associated with the user tool 110. The virtual boundary may be a boundary of a range of positions that the user tool 110 may occupy in order to comply with the simulated procedure, where the range of positions includes the target position. In some examples, the range of positions may represent the target position plus or minus a threshold distance from the target position. In some examples, the virtual boundary may change over a period of time according to the simulated procedure. For example, the simulated procedure may call for a movement of the first user tool 110. In some examples, the virtual boundary may be associated with a circle or even a pivot point within which the user tool should be moved during the procedure. In some examples, processing circuitry 102 may register the location of the first user tool 110 with respect to an arm or other device to which the first user tool 110 is attached. In this manner, sensors attached to the arm can track the location first user tool 110 based on arm movements.

Processing circuitry 102 may receive information indicative of a position of the portion of user tool 110 within operation envelope 130 (904). In some examples, the information indicates a position of first user tool 110 within an operation envelope, such as operation envelope 130. For example, operation envelope 130 may have one or more apertures configured to receive first user tool 110, where a user may move first user tool 110 within a space enclosed by a wall of operation envelope 130 to perform the simulated surgical procedure. One or more sensors (e.g., sensor(s)) 108) may detect the position of first user tool 110 in relation to operation envelope 130 and output the information indicative of the position to processing circuitry 102. In some examples, first user tool 110 may include one or more markers. Processing circuitry 102 may receive information form sensor(s) 108 which indicate a position of each respective marker of the one or more markers. Based on the position of each marker of the one or more markers, processing circuitry 102 may determine a position of the first user tool 110. For example, processing circuitry 102 may determine a depth and an angle of first user tool 110 within operation envelope 130.

In some examples, processing circuitry 102 is configured to compare the position of first user tool 110 within operation envelope 130 with the target position of first user tool 110 and/or the virtual boundary of first user tool 110 within the operation envelope 130. The target position of first user tool 110, in some cases, may be related to the simulated surgical procedure being performed using system 100. For example, a simulated surgical procedure may be associated with a "target trajectory" of first user tool 110, the target trajectory of first user tool 110 being similar to a movement of a surgical instrument during an authentic surgical procedure corresponding to the simulated surgical procedure. In some examples, processing circuitry 102 is configured to determine that the position of first user tool 110 within operation envelope 130 is displaced from the target position of user tool 110 within the enclosed space by greater than a threshold distance. Additionally, or alternatively, processing circuitry 102 is configured to determine that the position of first user tool 110 within operation envelope 130 is at the virtual boundary.

Processing circuitry controls, based on the position of the portion of first user tool 110, a haptic device to apply haptic feedback to first user tool 110 (906). In some examples, the haptic device may be part of first input device 140. In some cases, in response to determining that the position of first user tool 110 is outside of the virtual boundary, processing circuitry 102 is configured to cause the haptic device of first input device 140 to guide first user tool 110 to approach the target position of first user tool 110 within the space formed by the operation envelope 130. In this way, first input device 140 may correct mistakes made by the user during the simulated medical procedure. Additionally, or alternatively, in response to determining that the position of first user tool 110 is outside of the virtual boundary, processing circuitry 102 is configured to cause haptic device of the first input device 140 to apply a mechanical stimulus to first user tool 110. The mechanical stimulus may indicate to a user that the position of first user tool 110 is outside of the virtual boundary. In such cases, the first input device 140 may apply the mechanical stimulus to alert the user that the first user tool 110 is outside of the virtual boundary. In some examples, the haptic feedback applied to first user tool 110 by the haptic device prevents first user tool 110 from moving beyond the virtual boundary.

Processing circuitry 102 may receive user input that at least one of enables or disables control of the haptic device to apply haptic feedback to first user tool 110 based on the position of first user tool 110 in relation to the virtual boundary (908). In at least some examples where the haptic feedback applied to first user tool 110 by the haptic device prevents first user tool 110 from moving beyond the virtual boundary, disabling control of the haptic device to apply haptic feedback to first user tool 110 may allow first user tool 110 to move beyond the virtual boundary. Although the example operation of FIG. 9 is described with respect to first user tool 110 and first input device 140 of FIG. 1, the example operation of FIG. 9 may additionally or alternatively be performed using second user tool 120 and second input device 150.

Figure 10:
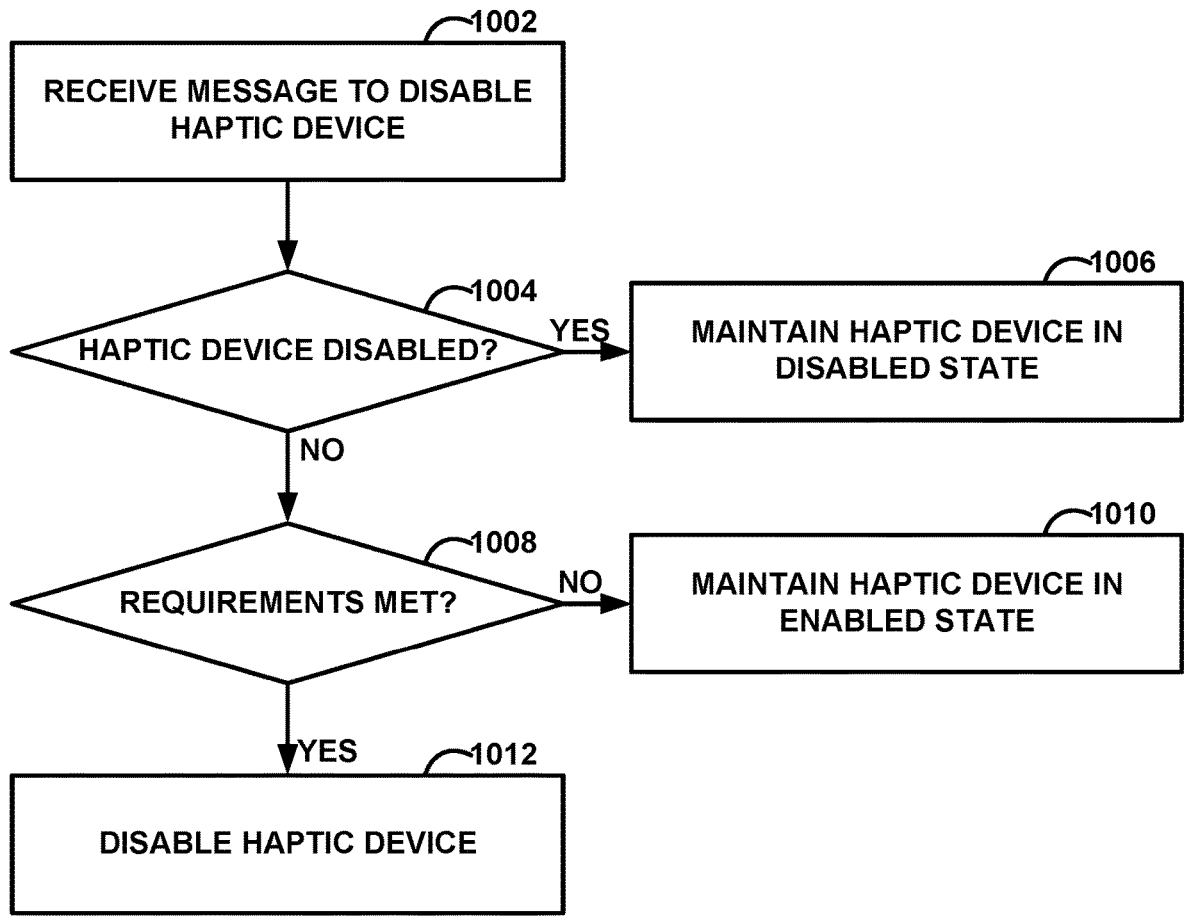
FIG. 10 is a flow diagram illustrating an example operation for disabling a haptic device, in accordance with one or more techniques of this disclosure.

FIG. 10 is a flow diagram illustrating an example operation for disabling a haptic device, in accordance with one or more techniques of this disclosure. For convenience, FIG. 10 is described with respect to system 100 of FIG. 1. However, the techniques of FIG. 10 may be performed by different components of system 100 or by additional or alternative medical devices.

Processing circuitry 102 may receive a message to disable a haptic device (1002), such as a haptic device of first input device 140. Processing circuitry 102 may determine whether the haptic device is disabled (1004). If the haptic device is disabled ("YES" branch of block 1004), processing circuitry 102 may maintain the haptic device in a disabled state (1006). If the haptic device is not disabled ("NO" branch of block 1004), processing circuitry 102 may determine if one or more requirements have been met (1008) in order to disable the haptic device. The haptic device may, in some examples, prevent a first user device 110 from moving outside of a virtual boundary. Additionally, or alternatively, the haptic device may output a mechanical stimulus in response to the first user device 110 from moving outside of the virtual boundary. In some examples, a user may decide to remove the haptic feedback in order to have a more realistic experience than examples in which the haptic feedback is enabled. The one or more requirements, in some examples, may include a minimum number of times to complete a simulated procedure, a minimum performance metric achievement, and/or or an approval by an administrator. For example, if a user has not completed a surgical procedure using system 100 at least a minimum number of times, processing circuitry 102 may determine that the one or more requirements have not been met.

If processing circuitry 102 determines that the one or requirements are not met ("NO" branch of block 1008), processing circuitry 102 may maintain the haptic device in the enabled state (1010). If processing circuitry 102 determines that the one or requirements are met ("YES" branch of block 1008), processing circuitry 102 may disable the haptic device (1012). Although the example operation of FIG. 10 is described with respect to first user tool 110 and first input device 140 of FIG. 1, the example operation of FIG. 10 may additionally or alternatively be performed using second user tool 120 and second input device 150.

The following numbered examples demonstrate one or more aspects of the disclosure.

Example 1. A simulator system for simulating one or more orthopedic procedures, where the simulator system includes: an input device configured to detect a position of a portion of a user tool within an operation envelope; a simulation device defining one or more surfaces that define one or more boundaries for a movement of the user tool within the operation envelope during a simulated surgical procedure; and processing circuitry configured to: receive, from the input device, information indicative of the position of at least the portion of the user tool within the operational envelope; generate a performance metric based on the position of at least the portion of the user tool within the operational envelope over a period of time; and output, for display to a user, the performance metric.

Example 2. The system of example 1, where the simulation device defines: an aperture configured to receive the user tool; a first channel extending from the aperture in a first direction, where the first channel is configured to receive the portion of the user tool responsive to a pivot of the user tool in the first direction; and a second channel extending from the aperture in a second direction, where the second channel is configured to receive the portion of the user tool responsive to a pivot of the user tool in the second direction.

Example 3. The system of examples 1-2 or any combination thereof, where the first direction forms an angle with the second direction at the aperture, and where the angle is within a range from 90 degrees to 180 degrees.

Example 4. The system of examples 1-3 or any combination thereof, where the first channel corresponds to a cut to be made in a surgical procedure corresponding to a simulated surgical procedure performed using the simulation device, and where the second channel corresponds to a cut to be made in a surgical procedure corresponding to the simulated surgical procedure performed using the simulation device.

Example 5. The system of examples 1-4 or any combination thereof, where at least some of a plastic material of the simulation device is deposited in a set of layers by a three-dimensional (3D) printer.

Example 6. The system of examples 1-5 or any combination thereof, where the plastic material includes any one or combination of nylon, acrylonitrile butadiene styrene (ABS), or polyethylene terephthalate (PETG).

Example 7. The system of examples 1-6 or any combination thereof, where a whole volume formed by a boundary of the plastic material of the simulation device is occupied by plastic material.

Example 7. The system of examples 1-7 or any combination thereof, where a portion of a volume formed by a boundary of the plastic material of the simulation device is not occupied by plastic material.

Example 9. The system of examples 1-8 or any combination thereof, where the simulation device represents a model of a desired modification of an anatomical structure.

Example 10. The system of examples 1-9 or any combination thereof, where the model of the desired modification of the anatomical structure includes a model of one or more cuts to one or more bones of a human body according to a simulated surgical procedure.

Example 11. The system of examples 1-10 or any combination thereof, where the model of one or more bones includes a model of one or more calcaneus bones.

Example 12. The system of examples 1-11 or any combination thereof, where the processing circuitry is configured to: generate, based on the position of the user tool within the operation envelope, visual information representing a position of the user tool in relation to a position of the one or more surfaces of the simulation device; and output, to a user interface, the visual information representing the position of the user tool in relation to the position of the one or more surfaces of the simulation device, where to generate the performance metric, the processing circuitry is configured to: generate the performance metric based on the visual information representing the position of the user tool in relation to the position of the one or more surfaces of the simulation device.

Example 13. A method for simulating one or more orthopedic procedures, where the method includes: detecting, by an input device, a position of a portion of a user tool within an operation envelope, where a simulation device defines one or more surfaces that define one or more boundaries for a movement of the user tool within the operation envelope during a simulated surgical procedure; receiving, by processing circuitry, information indicative of the position of at least the portion of the user tool within the operational envelope from the input device; generating, by the processing circuitry, a performance metric based on the position of at least the portion of the user tool within the operational envelope over a period of time; and outputting, by the processing circuitry for display to a user, the performance metric.

Example 14. The method of example 13, further including: receiving, by an aperture defined by the simulation device, the user tool; receiving, by a first channel extending from the aperture in a first direction, the portion of the user tool responsive to a pivot of the user tool in the first direction; and receiving, by a second channel extending from the aperture in a second direction, the portion of the user tool responsive to a pivot of the user tool in the second direction.

Example 15. The method of examples 13-14 or any combination thereof, where the first channel corresponds to a cut to be made in a surgical procedure corresponding to a simulated surgical procedure performed using the simulation device, and where the second channel corresponds to a cut to be made in a surgical procedure corresponding to the simulated surgical procedure performed using the simulation device.

Example 16. The method of examples 13-15 or any combination thereof, where the simulation device represents a model of a desired modification of an anatomical structure.

Example 17. The method of examples 13-16 or any combination thereof, where the model of the desired modification of the anatomical structure includes a model of one or more cuts to one or more bones of a human body according to a simulated surgical procedure.

Example 18. The method of examples 13-17 or any combination thereof, where the model of one or more bones includes a model of one or more calcaneus bones.

Example 19. The method of examples 13-18 or any combination thereof, further including: generating, by the processing circuitry based on the position of the user tool within the operation envelope, visual information representing a position of the user tool in relation to a position of the one or more surfaces of the simulation device; and outputting, by the processing circuitry to a user interface, the visual information representing the position of the user tool in relation to the position of the one or more surfaces of the simulation device, where generating the performance metric includes: generating the performance metric based on the visual information representing the position of the user tool in relation to the position of the one or more surfaces of the simulation device.

Example 20. A computer-readable storage medium storing instructions that, when executed, cause one or more processors to: detect a position of a portion of a user tool within an operation envelope, where a simulation device defines one or more surfaces that define one or more boundaries for a movement of the user tool within the operation envelope during a simulated surgical procedure; receive information indicative of the position of at least the portion of the user tool within the operational envelope from an input device; generate a performance metric based on the position of at least the portion of the user tool within the operational envelope over a period of time; and output, for display to a user, the performance metric.

Example 21. A simulator system for simulating one or more orthopedic procedures, the simulator system including: an input device configured to detect a position of at least a portion of a user tool within an operation envelope; a haptic device configured to apply haptic feedback to the user tool; and processing circuitry configured to: determine a virtual boundary for the user tool within the operation envelope, the virtual boundary representing a portion of a virtual bone; receive information indicative of the position of the portion of the user tool within the operation envelope; control, based on the position of the portion of the user tool within the operation envelope in relation to the virtual boundary, the haptic device to apply haptic feedback to the user tool; and receive user input that at least one of enables or disables control of the haptic device to apply haptic feedback to the user tool based on the position in relation to the virtual boundary.

Example 22. The system of claim 21, where the processing circuitry is further configured to compare the position of the portion of the user tool within the operation envelope with a target position of the portion of the user tool within the operation envelope.

Example 23. The system of claims 21-22 or any combination thereof, where the target position of the user tool within the operation envelope represents a target position of the user tool within the operation envelope over a period of time, and where the target position of the user tool within the operation envelope over a period of time represents a simulation of a surgical procedure associated with bone removal.

Example 24. The system of claims 21-23 or any combination thereof, where the processing circuitry is further configured to: determine that the position of the portion of the user tool is beyond the virtual boundary within the operation envelope, where the processing circuitry is configured to define the virtual boundary as the target position of the portion of the user tool plus a threshold distance from the target position.

Example 25. The system of claims 21-24 or any combination thereof, where the processing circuitry is configured to, in response to determining that the position of the portion of the user tool is beyond the virtual boundary, control the haptic device to provide a force to the user tool that prevents the user tool from moving beyond the virtual boundary within the operation envelope.

Example 26. The system of claims 21-25 or any combination thereof, where in response to determining that the position of the portion of the user tool is beyond the virtual boundary, the processing circuitry is configured to: control the haptic device to apply a mechanical stimulus to the user tool, where the mechanical stimulus indicates to the user that the position of the portion of the user tool is beyond the virtual boundary.

Example 27. The system of claims 21-26 or any combination thereof, where at least one of an amplitude of the mechanical stimulus or a frequency of the mechanical stimulus is correlated with a distance that the portion of the user tool is beyond the virtual boundary.

Example 28. The system of claims 21-27 or any combination thereof, where the processing circuitry is further configured to: track the position of the portion of the user tool within the operation envelope for a period of time; and generate, based on the position of the portion of the user tool within the operation envelope over the period of time, a performance metric indicating a performance level of a user.

Example 29. The system of claims 21-28 or any combination thereof, where in response to receiving the user input that disables control of the haptic device to apply haptic feedback to the user tool, the processing circuitry is configured to: control the haptic feedback device to remove a force against the user tool and allow the user tool to move beyond the virtual boundary, and where to track the position of the portion of the user tool within the operation envelope for a period of time, the processing circuitry is configured to: track at least one of a distance, an angle, or an amount of time that the portion of the user tool is beyond the virtual boundary, and where to generate the performance metric, the processing circuitry is configured to: generate the performance metric based on one of the distance, the angle, and the amount of time that the portion of the user tool is beyond the virtual boundary.

Example 30. The system of claims 21-29 or any combination thereof, where the user tool is a first user tool, the haptic device is a first haptic device, the input device is a first input device, the virtual boundary is a first virtual boundary, the portion of a virtual bone is a first portion of a virtual bone, and where the simulator system further includes: a second input device configured to detect a position of at least a portion of a second user tool within the operation envelope; and a second haptic device configured to apply haptic feedback to the second user tool, and where the processing circuitry is further configured to: determine a second virtual boundary for the second user tool within the operation envelope, the second virtual boundary representing a second portion of the virtual bone; receive information indicative of the position of the portion of the second user tool within the operation envelope; control, based on the position of the portion of the second user tool within the operation envelope in relation to the second virtual boundary, the second haptic device to apply haptic feedback to the second user tool; and receive user input that at least one of enables or disables control of the second haptic device to apply haptic feedback to the second user tool based on the position in relation to the second virtual boundary.

Example 31. The system of claims 21-30 or any combination thereof, where the processing circuitry is configured to: generate, based on the position of the user tool within the operation envelope, visual information representing a position of the user tool in relation to a position of the virtual bone; and output, to a user interface, the visual information representing the position of the user tool in relation to the position of the virtual bone.

Example 32. A method of simulating one or more orthopedic procedures, where the method includes: detecting, by an input device, a position of at least a portion of a user tool within an operation envelope; applying, by a haptic device, haptic feedback to the user tool; determining, by processing circuitry, a virtual boundary for the user tool within the operation envelope, the virtual boundary representing a portion of a virtual bone; receiving, by the processing circuitry, information indicative of the position of the portion of the user tool within the operation envelope; controlling, by the processing circuitry and based on the position of the portion of the user tool within the operation envelope in relation to the virtual boundary, the haptic device to apply haptic feedback to the user tool; and receiving, by the processing circuitry, user input that at least one of enables or disables control of the haptic device to apply haptic feedback to the user tool based on the position in relation to the virtual boundary.

Example 33. The method of example 32, where the method further includes: comparing the position of the portion of the user tool within the operation envelope with a target position of the portion of the user tool within the operation envelope.

Example 34. The method of examples 32-33 or any combination thereof, where the target position of the user tool within the operation envelope represents a target position of the user tool within the operation envelope over a period of time, and where the target position of the user tool within the operation envelope over a period of time represents a simulation of a surgical procedure associated with bone removal.

Example 35. The method of examples 32-34 or any combination thereof, further including: determining that the position of the portion of the user tool is beyond the virtual boundary within the operation envelope, where the processing circuitry is configured to define the virtual boundary as the target position of the portion of the user tool plus a threshold distance from the target position.

Example 36. The method of examples 32-35 or any combination thereof, further including: controlling, in response to determining that the position of the portion of the user tool is beyond the virtual boundary, the haptic device to provide a force to the user tool that prevents the user tool from moving beyond the virtual boundary within the operation envelope.

Example 37. The method of examples 32-36 or any combination thereof, where in response to determining that the position of the portion of the user tool is beyond the virtual boundary, the method further includes: controlling the haptic device to apply a mechanical stimulus to the user tool, where the mechanical stimulus indicates to the user that the position of the portion of the user tool is beyond the virtual boundary.

Example 38. The method of examples 32-37 or any combination thereof, further including: tracking the position of the portion of the user tool within the operation envelope for a period of time; and generating, based on the position of the portion of the user tool within the operation envelope over the period of time, a performance metric indicating a performance level of a user.

Example 39. The method of examples 32-38 or any combination thereof, where in response to receiving the user input that disables control of the haptic device to apply haptic feedback to the user tool, the method further includes: controlling the haptic feedback device to remove a force against the user tool and allow the user tool to move beyond the virtual boundary, and where tracking the position of the portion of the user tool within the operation envelope for the period of time includes: tracking at least one of a distance, an angle, or an amount of time that the portion of the user tool is beyond the virtual boundary, and where generating the performance metric includes: generating the performance metric based on one of the distance, the angle, and the amount of time that the portion of the user tool is beyond the virtual boundary.

Example 40. A computer-readable storage medium storing instructions that, when executed, cause one or more processors to: determine a virtual boundary for a user tool within the operation envelope, the virtual boundary representing a portion of a virtual bone; receive, from an input device configured to detect a position of at least a portion of the user tool within the operation envelope, information indicative of the position of the portion of the user tool within the operation envelope; control, based on the position of the portion of the user tool within the operation envelope in relation to the virtual boundary, a haptic device to apply haptic feedback to the user tool; and receive user input that at least one of enables or disables control of the haptic device to apply haptic feedback to the user tool based on the position in relation to the virtual boundary.

In one or more examples, the devices described herein may utilize hardware, software, firmware, or any combination thereof for achieving the functions described. Those functions implemented in software may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure.

Instructions may be executed by one or more processors. The one or more processors may, for example, include one or more DSPs, general purpose microprocessors, application specific integrated circuits ASICs, FPGAs, or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules configured for performing the techniques described herein. Also, the techniques could be fully implemented in one or more circuits or logic elements.

The techniques of this disclosure may be implemented in a wide variety of devices or apparatuses that include integrated circuits (ICs) or sets of ICs (e.g., chip sets). Various components, modules, or units are described in this disclosure to emphasize functional aspects of devices configured to perform the disclosed techniques, but do not necessarily require realization by different hardware units. Rather, various units may be combined or provided by a collection of interoperative hardware units, including one or more processors as described above, in conjunction with suitable software and/or firmware.

What is claimed is:

1. A simulator system for simulating one or more surgical procedures, wherein the simulator system comprises:
  memory; and
  processing circuitry communicatively coupled to the memory, the processing circuitry configured to:
    receive, from an input device configured to detect a position of at least a portion of a user tool within an operation envelope during a simulated surgical procedure, information indicative of the position of at least the portion of the user tool, wherein a simulation device includes a wall defining an aperture through which the portion of the user tool is configured to be received into the operation envelope, the simulation device defines a first channel extending from the aperture in a first direction and a second channel extending from the aperture in a second direction, the first channel is configured to receive the portion of the user tool responsive to a pivot of the user tool in the first direction, and the second channel is configured to receive the portion of the user tool responsive to a pivot of the user tool in the second direction;
generate a performance metric based on the position of at least the portion of the user tool over a period of time; and
output, for display to a user, the performance metric.

2. The simulator system of claim 1, wherein the first direction forms an angle with the second direction at the aperture, and wherein the angle is within a range from 90 degrees to 180 degrees.

3. The simulator system of claim 1, wherein the first channel corresponds to a first cut to be made in a surgical procedure corresponding to the simulated surgical procedure, and
wherein the second channel corresponds to a second cut to be made in the surgical procedure.

4. The simulator system of claim 1, wherein at least some of a plastic material of the simulation device is deposited in a set of layers by a three-dimensional (3D) printer.

5. The simulator system of claim 4, wherein a whole volume formed by a boundary of the plastic material of the simulation device is occupied by the plastic material.

6. The simulator system of claim 4, wherein a portion of a volume formed by a boundary of the plastic material of the simulation device is not occupied by the plastic material.

7. The simulator system of claim 1, wherein the simulation device represents a model of a desired modification of an anatomical structure.

8. The simulator system of claim 7, wherein the model of the desired modification of the anatomical structure includes a model of one or more cuts to one or more bones of a human body according to the simulated surgical procedure.

9. The simulator system of claim 8, wherein the model of one or more bones includes a model of one or more calcaneus bones.

10. The simulator system of claim 1, wherein the processing circuitry is configured to:
generate, based on the position of at least the portion of the user tool, visual information representing the position of at least the portion of the user tool in relation to a position of one or more surfaces of the simulation device; and
output, to a user interface, the visual information representing the position of at least the portion of the user tool in relation to the position of the one or more surfaces of the simulation device,
wherein to generate the performance metric, the processing circuitry is configured to generate the performance metric based on the visual information representing the position of at least the portion of the user tool in relation to the position of the one or more surfaces of the simulation device.

11. A method for simulating one or more surgical procedures, wherein the method comprises:
receiving, by processing circuitry, from an input device, information indicative of a position of at least a portion of a user tool within an operation envelope during a simulated surgical procedure, wherein a simulation device includes a wall defining an aperture through which the portion of the user tool is configured to be received into the operation envelope, the simulation device defines a first channel extending from the aperture in a first direction and a second channel extending from the aperture in a second direction, the first channel is configured to receive the portion of the user tool responsive to a pivot of the user tool in the first direction, and the second channel is configured to receive the portion of the user tool responsive to a pivot of the user tool in the second direction;
generating, by the processing circuitry, a performance metric based on the position of at least the portion of the user tool over a period of time; and
outputting, by the processing circuitry for display to a user, the performance metric.

12. The method of claim 11, wherein the first channel corresponds to a first cut to be made in a surgical procedure corresponding to the simulated surgical procedure, and
wherein the second channel corresponds to a second cut to be made in the surgical procedure.

13. The method of claim 11, wherein the simulation device represents a model of a desired modification of an anatomical structure.

14. The method of claim 13, wherein the desired modification of the anatomical structure includes a model of one or more calcaneus bones.

15. The method of claim 11, further comprising:
generating, by the processing circuitry based on the position of at least the portion of the user tool, visual information representing the position of at least the portion of the user tool in relation to a position of one or more surfaces of the simulation device; and
outputting, by the processing circuitry to a user interface, the visual information representing the position of at least the portion of the user tool in relation to the position of the one or more surfaces of the simulation device,
wherein generating the performance metric comprises:
generating the performance metric based on the visual information representing the position of at least the portion of the user tool in relation to the position of the one or more surfaces of the simulation device.

16. A non-transitory computer-readable storage medium storing instructions that, when executed, cause one or more processors to:
detect a position of at least a portion of a user tool within an operation envelope, wherein a simulation device includes a wall defining an aperture through which the portion of the user tool is configured to be received into the operation envelope during a simulated surgical procedure, wherein the simulation device defines a first channel extending from the aperture in a first direction and a second channel extending from the aperture in a second direction, the first channel is configured to receive the portion of the user tool responsive to a pivot of the user tool in the first direction, and the second channel is configured to receive the portion of the user tool responsive to a pivot of the user tool in the second direction;
receive information indicative of the position of at least the portion of the user tool from an input device;
generate a performance metric based on the position of at least the portion of the user tool over a period of time; and
output, for display to a user, the performance metric.

17. A simulator system for simulating one or more surgical procedures, wherein the simulator system comprises:
an input device configured to detect a position of a portion of a user tool relative to an operation envelope; and
a simulation device that includes a wall defining an aperture through which the portion of the user tool is configured to be received into the operation envelope during a simulated surgical procedure, the simulation device defines a first channel extending from the aperture in a first direction and a second channel extending from the aperture in a second direction, the first channel is configured to receive the portion of the user tool responsive to a pivot of the user tool in the first direction, and the second channel is configured to receive the portion of the user tool responsive to a pivot of the user tool in the second direction.

18. The simulator system of claim 17, wherein the first direction forms an angle with the second direction at the aperture, and wherein the angle is within a range from 90 degrees to 180 degrees.

19. The simulator system of claim 17, wherein the first channel corresponds to a first cut to be made in a surgical procedure corresponding to the simulated surgical procedure, and wherein the second channel corresponds to a second cut to be made in the surgical procedure.

20. The simulator system of claim 17, wherein the simulation device represents a model of one or more cuts to one or more bones of a human body according to the simulated surgical procedure.

* * * * *